US007005641B2

(12) United States Patent
Nakasuji et al.

(10) Patent No.: US 7,005,641 B2
(45) Date of Patent: Feb. 28, 2006

(54) ELECTRON BEAM APPARATUS AND A DEVICE MANUFACTURING METHOD BY USING SAID ELECTRON BEAM APPARATUS

(75) Inventors: Mamoru Nakasuji, Kanagawa (JP); Takao Kato, Tokyo (JP); Nobuharu Noji, Kanagawa (JP); Tohru Satake, Kanagawa (JP); Takeshi Murakami, Tokyo (JP); Kenji Watanabe, Kanagawa (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 10/731,163

(22) Filed: Dec. 10, 2003

(65) Prior Publication Data

US 2004/0119023 A1    Jun. 24, 2004

Related U.S. Application Data

(63) Continuation of application No. PCT/JP02/05786, filed on Jun. 11, 2002.

(30) Foreign Application Priority Data

| Jun. 15, 2001 | (JP) | ............... | 2001-181955 |
| Jun. 26, 2001 | (JP) | ............... | 2001-192597 |
| Sep. 6, 2001 | (JP) | ............... | 2001-269880 |
| Sep. 6, 2001 | (JP) | ............... | 2001-270935 |
| Sep. 10, 2001 | (JP) | ............... | 2001-273078 |

(51) Int. Cl.
*G21K 7/00* (2006.01)
(52) U.S. Cl. ................ 250/310; 250/311
(58) Field of Classification Search .......... 250/423 R, 250/427, 311, 310, 396 ML, 307
See application file for complete search history.

(56) References Cited

U.S. PATENT DOCUMENTS

| 3,777,211 | A |   | 12/1973 | Kuijpers ............... 315/31 R |
| 3,885,194 | A | * | 5/1975 | Schumacher ............ 315/107 |
| 4,363,995 | A | * | 12/1982 | Takigawa et al. ....... 313/346 R |
| 4,419,581 | A | * | 12/1983 | Nakagawa ........... 250/396 ML |

(Continued)

FOREIGN PATENT DOCUMENTS

JP         64-084629       3/1989

(Continued)

OTHER PUBLICATIONS

Technical Sales Solutions, LLC webpage, (describes the FEI 820 Dualbeam), May 11, 2005.*

(Continued)

*Primary Examiner*—John R. Lee
*Assistant Examiner*—Kalimah Fernandez
(74) *Attorney, Agent, or Firm*—Westerman, Hattori, Daniels & Adrian, LLP

(57) ABSTRACT

An electron beam apparatus, in which an electron beam emitted from an electron gun having a cathode and an anode is focused and irradiated onto a sample, and secondary electrons emanated from the sample are directed into a detector, the apparatus further comprising means for optimizing irradiation of the electron beam emitted from the electron gun onto the sample, the optimizing means may be two-stage deflectors disposed in proximity to the electron gun which deflects and directs the electron beam emitted in a specific direction so as to be in alignment with the optical axis direction of the electron beam apparatus, the electron beam emitted in the specific direction being at a certain angle with respect to the optical axis due to the fact that, among the crystal orientations of said cathode, a specific crystal orientation allowing a higher level of electron beam emission out of alignment with the optical axis direction.

9 Claims, 12 Drawing Sheets

U.S. PATENT DOCUMENTS

| | | | |
|---|---|---|---|
| 4,426,577 A * | 1/1984 | Koike et al. | 250/310 |
| 4,596,934 A * | 6/1986 | Yanaka et al. | 250/442.11 |
| 4,743,766 A | 5/1988 | Nakasuji et al. | 250/492.2 |
| 5,324,950 A * | 6/1994 | Otaka et al. | 250/441.11 |
| 5,389,787 A * | 2/1995 | Todokoro et al. | 250/310 |
| 5,811,819 A * | 9/1998 | Ohshima et al. | 250/423 R |
| 5,854,490 A | 12/1998 | Ooaeh et al. | 250/492.23 |
| 6,087,667 A | 7/2000 | Nakasuji et al. | 250/492.2 |
| 6,107,636 A | 8/2000 | Muraki | 250/492.2 |
| 6,162,735 A * | 12/2000 | Zimmermann et al. | 438/712 |
| 6,392,333 B1 * | 5/2002 | Veneklasen et al. | 313/361.1 |
| 6,465,792 B1 * | 10/2002 | Baptist | 250/396 R |
| 6,507,044 B1 * | 1/2003 | Santana et al. | 257/48 |
| 6,586,158 B1 * | 7/2003 | Dobisz et al. | 430/296 |
| 6,608,305 B1 * | 8/2003 | Kin et al. | 250/306 |
| 6,608,308 B1 * | 8/2003 | Takagi et al. | 250/311 |

FOREIGN PATENT DOCUMENTS

| | | |
|---|---|---|
| WO | WO 01/09922 A1 | 2/2001 |
| WO | WO 02/01596 A1 | 1/2002 |
| WO | WO 02/01597 A1 | 1/2002 |
| WO | WO 02/13227 | 2/2002 |
| WO | WO 02/37527 | 5/2002 |
| WO | WO 02/40980 | 5/2002 |

OTHER PUBLICATIONS

"The Detection and Measurement of Infra-Red Radiation" Smith et al.; 1968.

"Promising cathode materials for high brightness electron beams" J. Vac. Scl. Technol., B2(1), (1984), Shigeaki Zaima, et al.; pp73-79.

"Reduction Mechanism for Spherical and Chromatic Aberration Coefficients of Magnetic Lens and Retarding Electric Fields" JPN. J. Appl. Phys. vol. 32 (1993) M. Nakasuj et al.; pp4819-4825.

"Advance deflection concept for large area, high resolution e-beam lithography" J. Vac. Scl. Technol. 19(4) (1981), H.C. Pfeiffer, et al.; pp1058-10-63.

Electronic Beam Testing Handbook vol. 7 pp64-65, 3.3.A Shot Noise (with a partial English translation within brackets).

* cited by examiner

ELECTRON BEAM APPARATUS AND A DEVICE MANUFACTURING METHOD BY USING SAID ELECTRON BEAM APPARATUS

This application is a continuation of international application No.PCT/JP02/05786, filed on Jun. 11, 2002.

FIELD OF THE INVENTION

The present invention relates to an electron beam apparatus and a device manufacturing method by using the electron beam apparatus, and more specifically to an electron beam apparatus which can evaluate a sample containing a device pattern having a minimum line width not greater than 0.1 μm with high throughput and high reliability, and to a device manufacturing method which can improve a yield of products by using the electron beam apparatus to evaluate a wafer in the course of processing.

DESCRIPTION OF THE RELATED ART AND PROBLEMS TO BE SOLVED BY THE INVENTION

There has been suggested such an electron beam based inspection apparatus for inspecting defects in patterns formed on a surface of an object to be inspected, and more particularly, an inspection apparatus useful, for example, in inspecting defects on a wafer in a semiconductor manufacturing process, which includes irradiating an object to be inspected with an electron beam, detecting secondary electrons which vary in accordance with the properties of the surface thereof to form image data, and inspection patterns formed on the surface of the object to be inspected based on the image data at a high throughput, and a method of manufacturing devices at a high yield rate using the inspection apparatus.

In such an electron beam apparatus, in conjunction with a high integration of semiconductor device and a microfabrication of pattern thereof, an inspection apparatus with higher resolution and throughput has been desired.

So far, for example, there has been already suggested an electron beam apparatus in which an electron beam formed by focusing electron beam into fine flux is irradiated onto a sample so as to scan a surface thereof for evaluation; the sample having a device pattern with a line width not greater than 0.1 μm, wherein since an electron gun to be used in this kind of apparatus is required to produce the electron beam with a narrower diameter and a higher current, the temperature of a cathode is increased so that the electron gun may be used with an intensified brightness. Accordingly, the cathode is typically required to have such properties as including, a lower work function, a higher fusing point and a lower vapor pressure and also an excellent physical and chemical stability at high temperature. Conventionally, a mono-crystal of LaB6 has been used as a material having such properties, and the use of mono-crystal of tantalum carbide (TaC) is also under consideration.

In comparison between LaB6 and TaC, the work function is 2.6 eV for LaB6 and 3.4 eV for TaC, while to the contrary, a figure of merit (which is considered to be one of major measures for evaluating the material for the cathode and determined from the work function divided by a temperature at which the vapor pressure indicates to be $10^{-5}$ Torr, wherein a smaller figure of merit is considered more advantageous) is $1.27 \times 10^{-3}$ for LaB6 and $1.2 \times 10^{-3}$ for TaC, demonstrating that TaC is superior to LaB6. Accordingly, from the viewpoint of excellent stability at high temperatures, preferably TaC should be used as a material for making the cathode.

However, if a TaC chip is used to cause a field emission, due to the fact that among the crystal orientations of the TaC chip, a specific crystal orientation allowing a higher level of electron beam emission is not in alignment with an optical axis direction, such an intensified electron beam could not be emitted along a direction of the optical axis of the electron beam apparatus but emitted in directions at an angle of 19 degrees and an angle of 34 degrees symmetrically with respect to the optical axis by four times (i.e. 90 degrees spaced positions about the optical axis), respectively. Due to this, the use of the TaC chip has been problematic in that it can not be applied to the electron beam apparatus without modification.

Therefore, a first object of the present invention is to solve the above problem and to provide an electron beam apparatus, in which one of the electron beams emitted toward the directions other than the optical axis is guided in the direction of the optical axis with minimized aberration, whereby even such a material may be utilized as the cathode material, that has favorably a smaller figure of merit but has been considered difficult to be used as the material for making the cathode because of the reason that the intensified electron beam is not emitted in the direction of the optical axis.

Also, there has been known an apparatus for evaluating a sample containing MOS transistor with non-destructive method by using electron beam with high reliability, and also a device manufacturing method for evaluating a wafer by using the same apparatus each time respective processes are finished.

Such a technology has been known as an electron beam lithography system that uses an electron beam to raster-scan an entire surface of a sample, in which the beam is emitted exclusively onto a small region to be exposed but blocked to the other regions.

It has been also recognized in the trend of a gate oxide film of transistors becoming thinner and thinner every year that a large dose of electron beam may cause a potential difference between respective surfaces of the oxide film, sometimes leading to a dielectric breakdown.

In a prior-art defect inspection apparatus (an electron beam apparatus) using an electron beam, the electron beam has been irradiated over an entire region of a limited area of a sample wafer, to detect secondary electrons.

In the prior-art defect inspection apparatus using the electron beam, however, there arises a problem that if the gate oxide film with a thickness of 1 nm or less is subjected to a relatively high dose level of electron beam, non-negligible probability of breakdown of the oxide film could be caused by the electron beam irradiation. On the other hand, there has been a problem, however, that if the dose level of the electron beam is insufficient, a signal could not have sufficient S/N ratio in forming the image, which leads to a failure in accomplishing a highly reliable defect inspection.

Accordingly, a second object of the present invention is to provide an electron beam apparatus which enables a highly reliable evaluation, including a defect inspection, to be carried out without causing any breakdowns in a portion of the sample, such as the gate oxide film or the like.

Further, in the field of electron beam apparatus for inspecting a sample for any defects, there has been known an electron beam apparatus that uses a TFE electron gun and focuses an electron beam therefrom into a crossover on a sample thus to scan a surface thereof and to detect secondary electrons emanated from the sample.

In such an electron beam apparatus, if the TFE electron gun is used, a beam current as high as 100 nA is obtainable with a beam diameter of 100 nm, and if it is driven by a clock of 100 MHz, then a shot noise, $I_N$, for a secondary electron yield η of 50%, will be expressed as;

$$i_N = (2\eta \times i_b \times \Delta f)^{1/2}$$
$$= (2e \times 50 \times 10^{-9} \times 100 \times 10^6)^{1/2}$$
$$= 1.265 \times 10^{-9} A,$$

(where, e=charge of an electron, $i_b$=a beam current, and Δf=a frequency band of a secondary electron detector) and accordingly, a S/N ratio will be expressed as;

$$S/N = i_b / i_N$$
$$= 50 \times 10^{-9} / 1.265 \times 10^{-9}$$
$$= 39.5,$$

which can not satisfy a condition of S/N>45 required to perform an defect inspection or the like, and consequently scanning should be repeated by several times and then an averaging and adding operation applied.

Accordingly, a third object of the present invention is to provide an electron beam apparatus in which a beam is obtainable that enables a resolution of 100 nm to be obtained with the condition of S/N>45 for the scanning at 100 MHz without the need for the averaging and adding operation.

Further, conventionally, it has been known that an electron beam apparatus employing an objective lens of a decelerating electric field type is useful, because it can effectively reduce an axial chromatic aberration coefficient and a spherical aberration. On the other hand, it has been also well known that, if an objective lens of a non-decelerating electric field type is used, it may be possible to evaluate a wafer over a surface including its edge portion.

However, there has been such a problem with the electron beam apparatus comprising the objective lens of the above-mentioned decelerating electric field type, in which a decelerating electric filed is produced between the objective lens and the wafer, that if the edge portion of the wafer is located adjacent to an optical axis, an aberration is induced by turbulence in the electric field caused by the peripheral edge of the wafer, which leads to an erroneous evaluation. Specifically there has been such a problem in the case of evaluating a pattern with dimensions not greater than 0.1 μm, which is commonly used nowadays, that the evaluation is effective only for a region defined as an inner side with respect to the peripheral edge of the wafer by a distance not smaller than 15 mm.

On the other hand, there has also been a problem with a use of the objective lens of the non-decelerating electric field type that the axial chromatic aberration is rather intensified and if the beam is converged to be made narrower, then a beam current may be greatly lowered.

Therefore, a fourth object of the present invention is to provide an electron beam apparatus which can evaluate any region of the wafer requiring an evaluation without any effect from the chromatic aberration by using an objective lens having a smaller axial chromatic aberration coefficient.

It has been conventionally known that a shot noise, $i_f^2$, in the case of a current of $I_0$ being applied to an infra-red detector can be expressed by an equation;

$$\overline{i_f^2} = 2e \cdot I_0 \cdot \Gamma^2 \cdot \Delta f$$

and that if an electron gun is under a temperature limited condition, said Γ is 1.0, and if the electron gun is under a space charge limited condition, said Γ falls in a range of 0.1 to 1.0 (see R. A. Smith, et. al, "*The Detection and Measurement of Infra-red Radiation*" Oxford at the Clarend on Press 1968, p 195).

Further, it has been known that a shot noise, $i_n^2$, as a electron tube noise is expressed by an equation;

$$\overline{i_n^2} = \Gamma^2 \cdot 2e \cdot I_p \cdot B_f$$

where, $i_n^2$=a mean square of a noise current, e=charge of an electron, $I_p$=an anode current, and $B_f$=a frequency band of a signal amplifier, and said $\Gamma^2$ is a decreasing function with respect to a cathode temperature $T_k$, for which a value in a range of 0.16 to 0.018 has been actually measured (see "*Communication Engineering Handbook*" edited by Institute of Telecommunications Engineers, p 471, 1957).

However, so far as the signal detection in the electron beam apparatus is concerned, the information with regard to the infra-red technology and the electron tube technology has not been utilized effectively, and the shot noise has been treated as Γ=1. Besides, in spite of the fact that if the cathode temperature of the electron gun is increased, the shot noise could be decreased, the cathode temperature has been determined in practice without taking the shot noise into account.

Accordingly, a fifth object the present invention is to provide an electron beam apparatus which can decrease the shot noise and thus increase the S/N ratio by determining the cathode temperature with the shot noise taken into account, so that the secondary electrons or the likes emanated from the sample may be detected efficiently.

Another object of the present invention is to provide a device manufacturing method aiming for improving inspection accuracy and throughput by using said electron beam apparatus to inspect a semiconductor device in the course of processing or to inspect a finished product.

SUMMARY OF THE INVENTION

The objects of the above described may be accomplished by the features of the present invention, which comprises an electron beam apparatus, in which an electron beam emitted from an electron gun having a cathode and an anode is focused and irradiated onto a sample and secondary electrons emanated from the sample are directed into a detector, wherein the electron beam apparatus characterized in further comprising means for optimizing irradiation of the electron beam emitted from the electron gun onto the sample.

By these arrangements, the problems described above may be dissolved and thereby irradiation efficiency of the electron beam onto the sample is increased and, thus, S/N ratio of the electron beam apparatus is improved, which results in high throughput and high reliability of the electron beam apparatus.

More specifically, the first object of the present invention described above may be accomplished by the first invention of the present invention, wherein the electron beam apparatus is constituted in such a way that an electron beam emitted from an electron gun having a cathode and an anode is focused and irradiated onto a sample and secondary electrons emanated from said sample are directed into a detector, wherein the optimizing means includes two-stage deflectors disposed in the proximity to the electron gun, wherein the two-stage deflectors are adapted so as to deflect and direct an electron beam emitted in a specific direction so as to be in alignment with an optical axis direction, the electron beam emitted in the specific direction being at a certain angle with respect to the optical axis due to the fact that, among crystal orientations of the cathode, a specific crystal orientation allowing a higher level of electron beam emission is out of alignment with the optical axis direction. With this configuration, it is possible to orient one of the electron beams emitted in the specific directions other than that of the optical axial, so as to be in alignment with the optical axial direction while minimizing any aberration.

Further, in one mode of the first invention, one deflector of the two-stage of deflectors, which has been disposed in a closer location to the electron gun, is designed to be an electromagnetic deflector and the other deflector of the two-stage deflectors, which is disposed in a closer location to the sample, is designed to be an electrostatic deflector. This configuration enables the electron beams emitted in the direction other than that of the optical axis to be guided into the optical axial direction without causing any chromatic aberrations.

In another mode of the first invention, the crystal of the cathode is defined as such crystal that is composed of carbide, boride or nitride of transition metals.

According to a further aspect of the first invention, the electron beam apparatus is constituted as a one, in which an electron beam emitted from an electron gun is focused and irradiated into a sample and a secondary electrons emanated from the sample are directed into a detector, wherein the optimizing means comprises the cathode, an anode having a potential near to that of the cathode and the anode, wherein only an electron beam that has been emitted in a particular direction among a plurality of electron beams emitted in different directions from the electron gun is directed onto the sample, and the electron beams emitted in the directions other than the particular direction are absorbed into said anode having potential near to that of the cathode and thus discarded.

In order to accomplish the second object described above, according to the second invention, the electron beam apparatus is constituted in such a way that an electron beam is irradiated against a sample and secondary electrons emanated from an electron beam irradiated region on a surface of the sample are detected so as to evaluate the sample, wherein the sample has a partial region on the surface thereof which is relatively week against or susceptible to dielectric breakdown possibly caused by electron beam irradiation, wherein the optimizing means is constituted as means for controlling irradiation of the electron beam so as not to irradiate the susceptible region but to irradiate the other regions exclusively.

In the electron beam apparatus of the second invention, a region having a gate oxide film of transistor formed thereon and a region having an electric connection with the region of gate oxide film may be selected as the region relatively weak against dielectric breakdown.

Further, in the electron beam apparatus of the second invention, a scanning operation of the electron beam may be adapted to be applied over an entire surface of the sample, but the electron beam may be blanked when the electron beam is to scan the region relatively weak against dielectric breakdown.

According to another aspect of the second invention, when a surface of a sample is segmented into a region relatively weak against dielectric breakdown and the other regions, the optimizing means is constituted as means for controlling the irradiation of the electron beam so that a different dose level of electron beam is applied to each of the respective different regions so as to evaluate the surface of the sample.

In order to accomplish the third object of the present invention, according to the third invention of the present invention, the electron beam apparatus is constituted in such a way that an electron beam emitted from an electron gun having a hot cathode is irradiated against an aperture and the electron beam after having passed through the aperture is contracted and projected onto a sample, two-stage of deflectors are operated to scan the sample, and secondary electrons emanated from the sample are accelerated by an electric field produced by an objective lens and guided by an E×B separator into a secondary electron detector, wherein the optimizing means is constituted as means for setting a pivot point of deflection by the two-stage of deflectors in such a location that can minimize a transverse chromatic aberration in the proximity of said objective lens.

In the second invention, the electron gun can be operative under a space charge limited condition. In addition, the aperture can be formed in a square shape. Furthermore, a negative voltage can be applied to the sample and a voltage having a lower potential than that of the sample can be applied to a lower electrode of the objective lens.

In order to accomplish the fourth object of the present invention described above, according to the fourth invention of the present invention, the electron beam apparatus comprises an electron optical system which produces a decelerating electric field for a primary electron beam between an objective lens and a sample so that a focused electron beam can scan a surface of the sample, in which secondary electrons emanated from said sample, after having passed through the objective lens, are deflected from the electron optical system so as to be detected, wherein the optimizing means is constituted as means for establishing such a dimensional relationship as represented by an expression:

$$W+D/2 \leq 5 \text{ mm}$$

where "W" is a working distance of the objective lens, and "D" is a bore diameter of an electrode of the objective lens disposed in a closest location to the sample.

According to the fourth invention as described above, since the objective lens has been designed based on the above expression, at least a region of a sample subject to the inspection defined as an inner side with respect to the peripheral edge of the sample by a distance not smaller than 5 mm is substantially free from the interference of the turbulence in the electrostatic field caused by the peripheral edge of the sample, and thereby the sample can be evaluated in that region with high accuracy in the lower aberration condition. Since, typically, chips larger than 5 mm squares are fabricated in most cases, with the apparatus according to the fourth invention which can evaluate a region 5 mm or more distant from a peripheral edge of a wafer, almost all samples can be properly handled for accurate evaluation.

According to the second aspect of the second invention, the electron beam apparatus is composed to be able to evaluate a flat wafer within a range defined as an inner side with respect to a periphery of the wafer by a distance not less than "R" mm, by using an electron optical system having an objective lens of a decelerating electric field type, wherein the optimizing means is constituted as a means for establishing such a dimensional relationship as represented by an expression:

$$W+D/2 \leq R \text{mm}$$

where "W" is a working distance of the objective lens, and "D" is a bore diameter of an electrode of the objective lens disposed in location closest to said sample.

According to the second aspect of the second invention, since the objective lens has been designed based on the basis of above expression, at least a region of a sample subject to the inspection defined as an inner side with respect to the peripheral edge of the sample by a distance not smaller than "R"mm is substantially free from interference of the turbulence in the electrostatic field caused by the peripheral edge of the sample, and thereby the sample can be evaluated in that region with high accuracy in the lower aberration condition. Further, it can be seen from the above expression that as the bore diameter "D" reduced, a smaller value for "R" may be determined to extend the region subject to the inspection, and thus an outer diameter of the objective lens can be reduced.

According to a third aspect of the second invention, in accordance with either one of the above-described aspects, at least the objective lens has an electrode of axisymmetric structure made of an insulating material with a metal coating applied selectively onto a surface thereof.

According to the third aspect of the second invention, the diameter of the objective lens may be further reduced, whereby a diameter of a optical column for accommodating the electron optical system can be made smaller.

According to a fourth aspect of the second invention, a plurality of electron optical systems having the features of either one of the above described aspect is arranged in parallel above a sheet of sample. With this configuration, since different electron images for different regions on the sample can be obtained in respective electron optical systems, the throughput of the sample inspection may be improved in proportion to the number of employed electron optical systems. In the above respective aspects of the present invention, in which the diameter of the objective lens can be adaptively made smaller in design, a plurality of electron optical systems can be accommodated in parallel, and the third aspect of the present invention is especially preferable, in which the diameter of the objective lens can be made smallest.

In order to accomplish the fifth object of the present invention, according to the fifth invention, the electron beam apparatus has an electron optical lens column configured such that an electron beam emitted from a thermionic emission cathode may be irradiated against a sample and either one of secondary electrons, back scattered electrons or absorbed electrons, which has been emanated from the sample, may be focused onto a detecting system, wherein the optimizing means is constituted as means for determining a value for a heating electric power of the thermionic emission cathode by evaluating a signal/noise ratio or a noise level detected in the detecting system during a period when said electron beam is irradiated against the sample while changing a heating electric power of the thermionic emission cathode.

According to a second aspect of the fifth invention, a value for the heating electric power of the thermionic emission cathode can be determined in such a manner that a signal/noise ratio exceeds a predetermined value, or such that a noise level is not greater than a predetermined value when a certain level of beam current is applied to the sample from the electron beam emitted from the thermionic emission cathode.

According to a third aspect of the fifth invention, the value for the heating electric power of the thermionic emission cathode can be determined in such a manner that an increase in rate of the signal/noise ratio with respect to the heating electric power is not greater than a predetermined value, or a decreasing rate of said noise level is not greater than a predetermined value when a certain level of beam current is applied to the sample from the electron beam emitted from the thermionic emission cathode.

According to a fourth aspect of the fifth invention, the value for the heating electric power of said thermionic emission cathode may be determined by evaluating a noise current/beam current ratio.

According to a fifth aspect of the fifth invention, the value for the heating electric power of the thermionic emission cathode may be roughly tuned in such a manner that a variation in an electron gun current observed during a period when the heating electric power of the thermionic emission cathode is changed may be moderate, and following this roughly tuning, the value for the heating electric power of the thermionic emission cathode can be finely tuned based on an evaluation of the signal/noise ratio or the noise level detected in the detecting system.

According to a sixth aspect of the fifth invention, the value for the heating electric power of the thermionic emission cathode can be determined in consideration of a relationship between the heating electric power of the thermionic emission cathode and the signal/noise ratio and another relationship between the heating electric power of the thermionic emission cathode and a lifetime of the thermionic emission cathode.

According to a sixth invention, a device manufacturing method may be implemented, which is characterized by evaluating a wafer in the course of processing or after completion of processing by using either one of the electron beam apparatuses described above.

These and other aspects and actions and effects of the present invention may be further understood by reading the following description with reference to the attached drawings.

DESCRIPTION OF THE PREFERRED EMBODIMENTS

Preferred embodiments of an electron beam apparatus according to the present invention will be described below with reference to the attached drawings.

Embodiments of a First Invention

Figure 1:
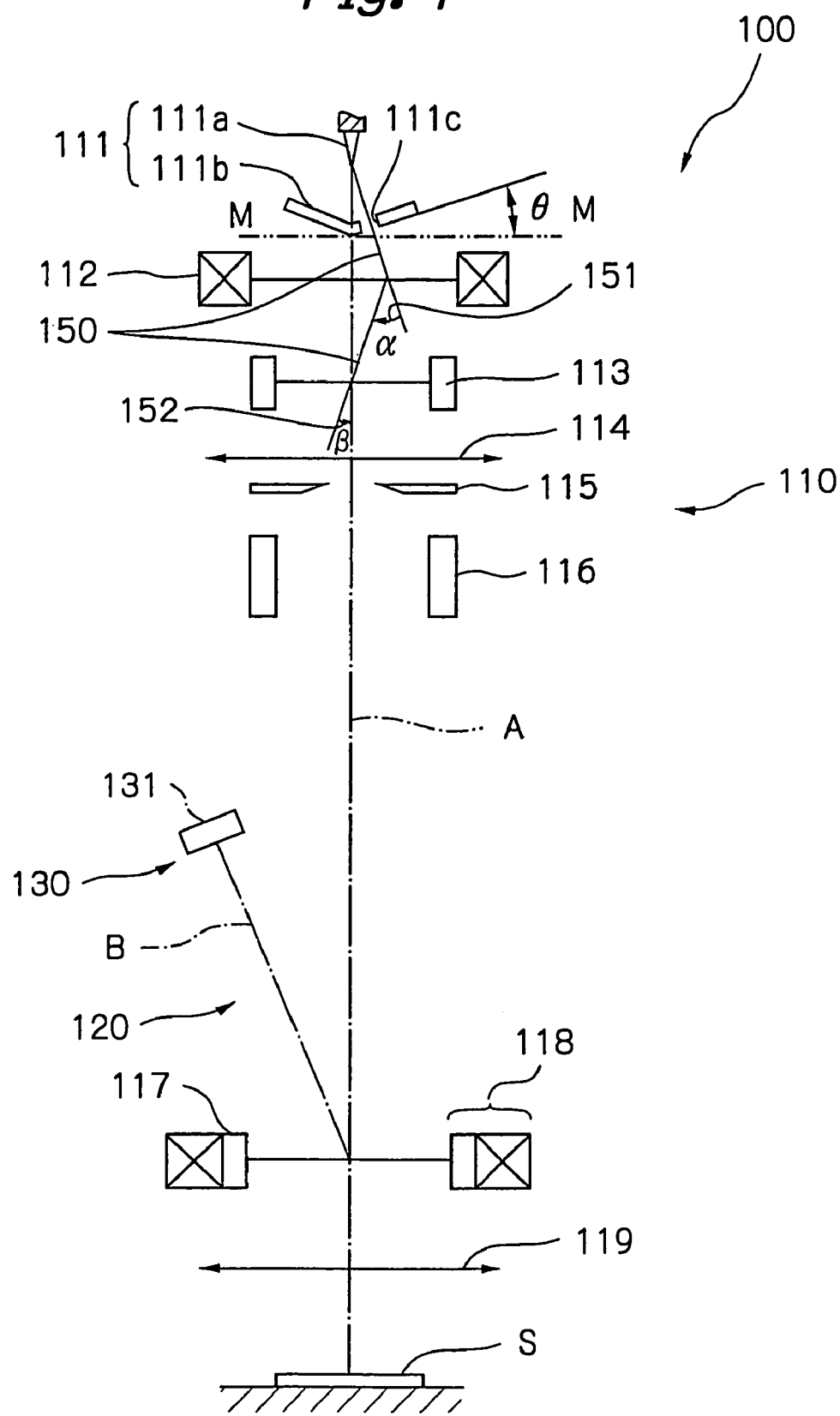
FIG. 1 is a schematic diagram of an optical system of an electron beam apparatus according to an embodiment of a first invention of the present invention.

FIG. 1 schematically shows an electron beam apparatus 100 of an embodiment according to a first invention of the present invention. This electron beam apparatus 100 comprises a primary optical system 110, a secondary optical system 120 and an inspection unit 130. The primary optical system 110 is an optical system for irradiating an electron beam against a surface of a sample S (a sample surface), and comprises an electron gun 111 for emitting the electron beam, an electromagnetic deflector 112 and an electrostatic deflector 113 for deflecting the electron beam emitted from the electron gun, a condenser lens 114 for focusing the electron beam, an aperture 115 defining an numerical aperture, electrostatic deflectors 116 and 117 for controlling the electron beam so as to scan a surface of the sample, an E×B separator 118 and an objective lens 19, wherein those components described above are arranged along an optical axis "A" of the primary optical system 110 in a sequential order with the electron gun 111 at the topmost location as shown in FIG. 1.

In the electron gun 111, a mono-crystal TaC cathode of <100> orientation is employed as a thermal field emission (TFE) cathode 111a, and an anode 111b is used to draw out the electron beam. Since the emission direction of the electron beam is defined at the angle of about 18.5° with respect to the optical axis A, the anode 111b is formed in a conical shape inclined at an angle θ of 18.5° with respect to a plane M—M normal to the optical axis A and is provided with an aperture 111c formed therein for allowing one of the four beams to pass through.

The secondary optical system 120 is arranged along an optical axis B inclined with respect to the optical axis A of the primary optical system 110 in a location proximal to the E×B separator 118 of the primary optical system 110.

The inspection unit 130 comprises a detector 131.

In the electron beam apparatus as described above, the electron beam emitted from the cathode 111a of the electron gun 111 is accelerated by an anode 111b, and the electron beam 150, after having exited from the aperture 111c of the anode, is deflected at an angle of deflection α into the direction indicated by the arrow 151 (i.e. toward the optical axial direction) by the electromagnetic deflector 112 and further deflected back at an angle of deflection β in the direction indicated by the arrow 152 by the electrostatic deflector 113, so that the electron beam 150 may be oriented in the direction in alignment with the optical axis A. In this way, the electron beam 150, which has been emitted in the direction at a certain angle with respect to the optical axis, due to the fact that among the crystal orientations of the mono-crystal TaC cathode, a specific crystal orientation allowing a higher level of electron beam emission is out of alignment with said optical axis direction, can be oriented in a direction in alignment with the optical axial direction (i.e., directed along the optical axial direction) by using the two-stage of deflectors 112 and 113.

The electron beam is then focused by the condenser lens 114 to be formed into a crossover in the electron gun side of the objective lens 119 and further focused by the objective lens 119 onto the sample S. At that time, the electron beam is deflected by the electrostatic deflector 116 and the electrostatic deflector 117 of the E×B separator 118 and irradiated onto the sample S so as to scan the surface thereof.

The secondary electrons emanated from the sample S by the irradiation of this electron beam are accelerated and focused by an accelerating electric field applied between the objective lens 119 and the sample S, and then pass through the objective lens 119. The secondary electrons, after having passed through the objective lens, are deflected by the E×B separator 118 in the direction in alignment with that of the optical axis B and then detected by the detector 131 of the inspection unit 130 for evaluating the sample S.

In such an electron beam apparatus as described above, it is required to reduce any chromatic aberration caused by the deflection in the two-stage of deflectors in order to improve a resolution of the optical system. To achieve this, a distance between a tip end portion of the cathode 111a and the electromagnetic deflector 112 is set to be equal to a distance between the electromagnetic deflector 112 and the electrostatic deflector 113, thereby making the angle of deflection α twice that of the angle of deflection β and thus reducing chromatic aberration caused by the deflection. Although the TaC is favorable from the fact that if the TaC is used, since an angular current density value as large as 10 mA/sr can be obtained, the electron beam of 800 nA with 100 nmφ is obtainable, yet the crystal of the cathode is not limited to this but may be a crystal of other transition metals composed of carbide, boride or nitride.

Further, it is also possible to appropriately change the number of deflectors, the angle of inclination θ of the anode 111b, and the location of the aperture 111c of the anode, depending on the kinds of the transition metals employed, so that only an electron beam that has been emitted in a specific direction among a plurality of electron beams emitted in different directions can be guided onto the sample S and those electron beams emitted in the directions other than the specific direction may be all discarded.

Figure 2:
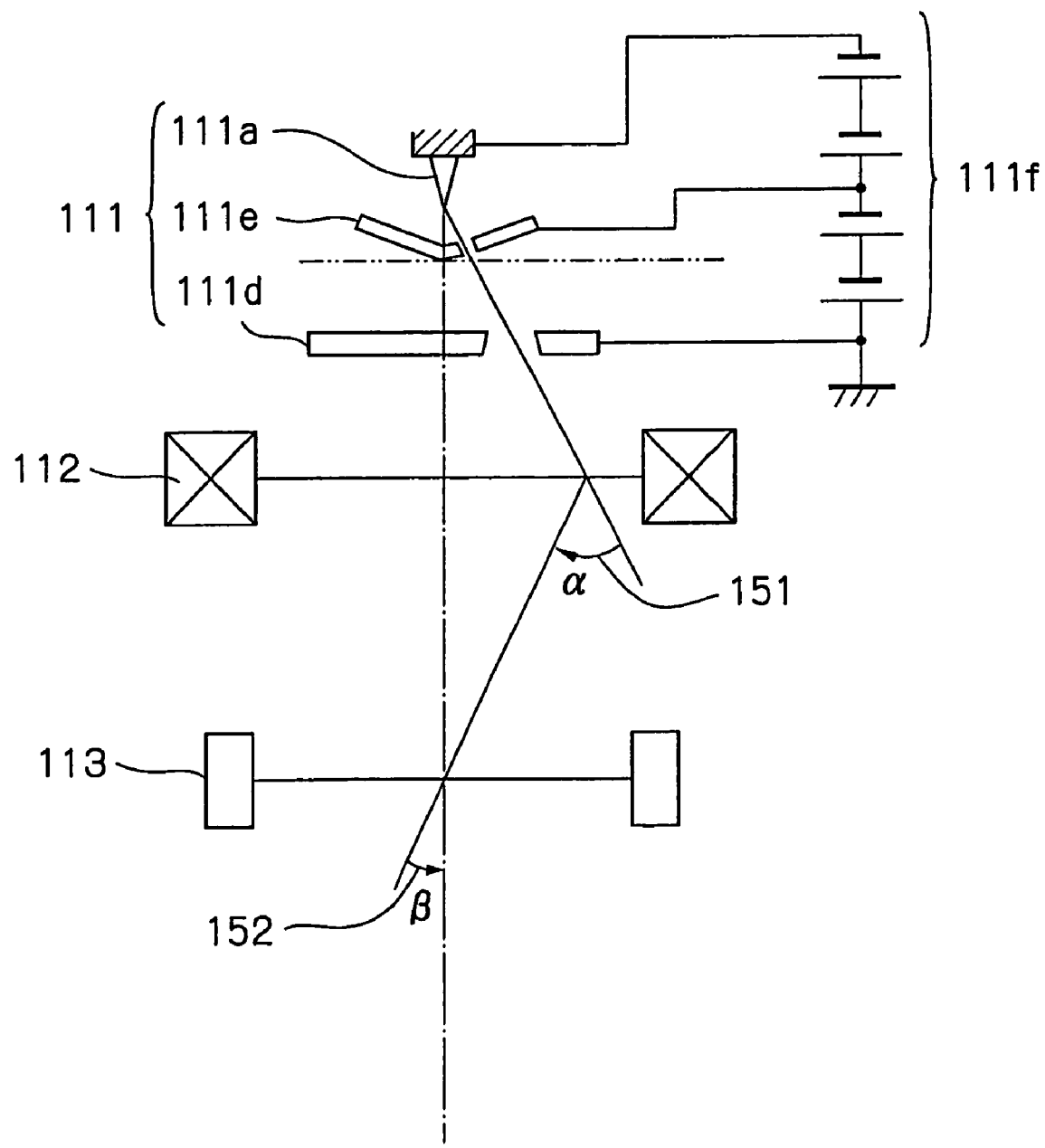
FIG. 2 is a schematic diagram of the main parts of an optical system of an electron beam apparatus according to another embodiment of the first invention of the present invention.

FIG. 2 shows a second embodiment of the first invention. In this embodiment, a condenser lens, an aperture, an electrostatic deflector, an E×B separator and an objective lens included in a primary optical system, respective components included in a secondary optical system and an inspection unit, all of them have the same configurations as those of the first embodiment, and accordingly those components are omitted in FIG. 2 but only the components different from those of the first embodiment are shown in FIG. 2. In addition, such components as equivalent to those of the first embodiment are designated with the same reference numerals. In this embodiment, an anode of an electron gun 111 has a unique configuration, in which an anode 111e having a potential near to that of a cathode 111a is independently provided in addition to a typical anode 111d so as to form a two-stage of anodes 111d and 111e. The anode 111e has been made in a similar form to the anode 111b of the first embodiment. In such a configuration, those electron beams emitted from the cathode 111a in the direction of discarding are absorbed into the anode 111e having a potential near to that of the cathode. Thereby, heat generated in the anode may be reduced, which allows a small capacity of power supply 111f to be used for the electron gun. Other operations of the electron beam apparatus according to this embodiment are similar to those explained with reference to the first embodiment of FIG. 1.

Incidentally, in the second embodiment described above, the electrostatic deflectors 112 and 113 are not necessarily indispensable since a specific crystal orientation allowing a higher level of electron beam emission can be selected so as to be in alignment with the optical direction.

According to the first invention described above, advantageously the following effects can be obtained.

(1) An intensified electron beam obtained by means of a mono-crystal TaC cathode may be effectively guided to an optical axis of a primary optical system.

(2) Since an electron beam with a beam size of 100 nm$\phi$ and an electron beam current of 800 nA is obtainable, the throughput of the electron beam apparatus can be improved.

(3) The electron beam can be deflected at an angle in the range of 38° without substantially causing chromatic aberration.

(4) With a use of TaC, which has a smaller figure of merit as compared to LaB6, such an electron gun having a longer operating life and an intensified brightness can be obtained.

(5) As is the case in the second embodiment, if an anode is provided in the form of two-stage of anodes, majority of emission current can be absorbed into an anode having a potential near to that of the cathode and accordingly heat generation in the anode can be reduced, which allows a smaller capacity of power supply for the electron gun to be employed.

Embodiments of a Second Invention

Figure 3:
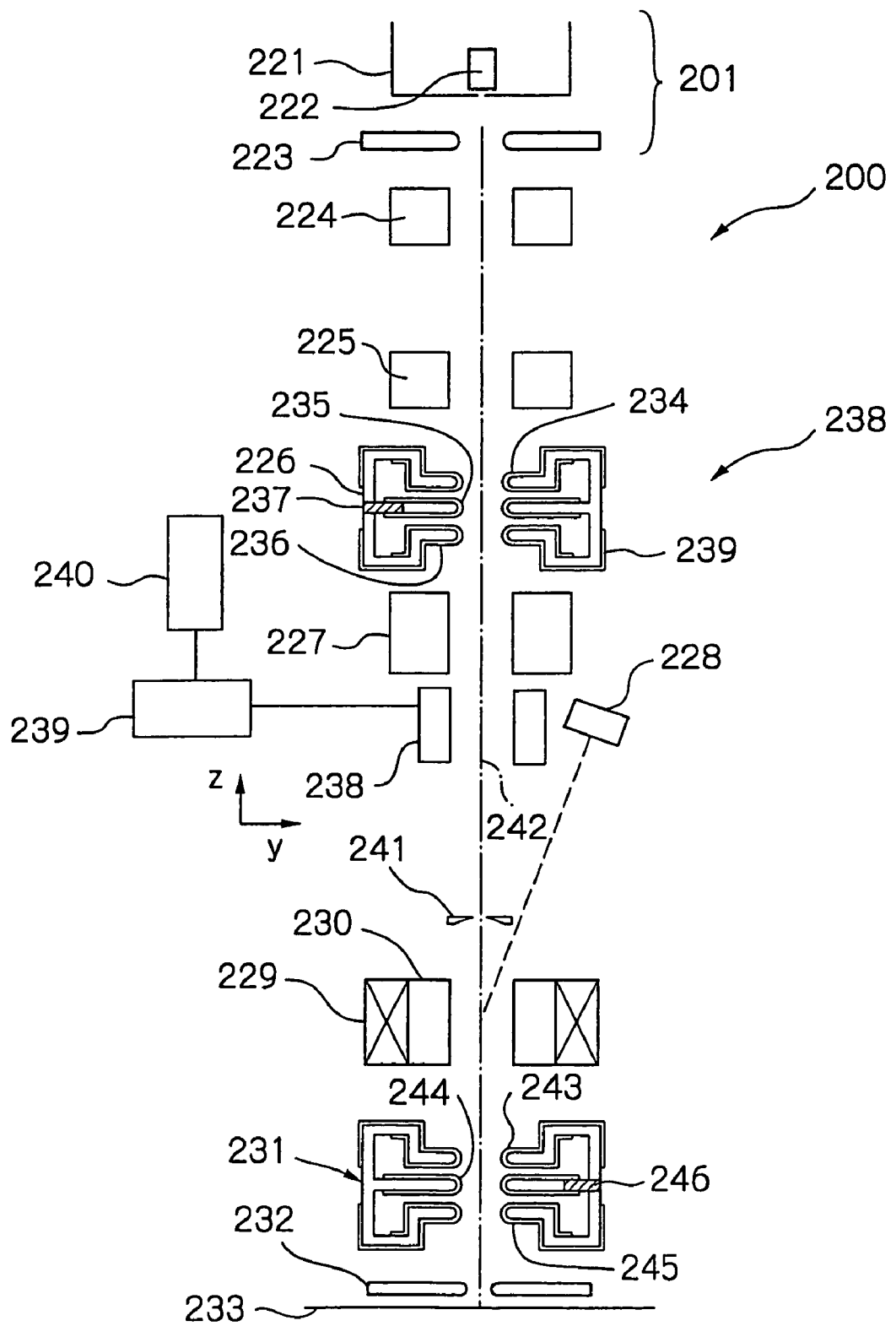
FIG. 3 is a schematic diagram of an electron beam apparatus according to an embodiment of a second invention of the present invention.

FIG. 3 is a schematic diagram of an electron beam apparatus according to an embodiment of a second invention of the present invention.

The electron beam apparatus 200 according to the present embodiment comprises a three-electrode type electron gun 201 comprising a Wehnelt 221, a cathode 222 and an anode 223, for emitting a primary electron beam; axial aligning electrostatic deflectors 224, 225 for aligning an axis of the primary electron beam with respect to a subsequent lens; a condenser lens 238; an electrostatic deflector 227; an E×B separator (229, 230); an objective lens 231; an axisymmetric electrode 232; and a detector 228 for detecting a secondary electron beam emanated from a sample 233. The sample 233 is mounted on a stage for transferring the sample 233 within an X-Y plane. By way of this, secondary electron images of the sample 233 for an overall region to be inspected can be obtained.

An electron beam emitted from the electron gun 201 is focused by the condenser lens unit 238 so as to form a crossover in a deflection center 242 of a blanking deflector 238, and then is further focused by the objective lens 231 to form a small spot on a surface of the sample 233. The deflector 227 and an electromagnetic deflector 229 within an E×B separator 229, 230 function cooperatively to deflect the beam so as to raster-scan the sample 233. Secondary electrons emanated from scanned points of the sample 233 are accelerated and focused by an accelerating electric field produced by the objective lens 231, deflected by the E×B separator 229, 230 in the right hand direction in FIG. 3, and then detected by the secondary electron detector 228, which combines the detection result with a scanning signal to form a SEM image. It is to be noted that prior to this image formation, registration should be performed so as to determine accurately which location on the sample 233 is being scanned.

The axisymmetric electrode 232 disposed between the objective lens 231 and the sample 233 is functioning for providing a voltage further lower than a voltage on the sample surface and thereby partially decreasing an axial potential to a lower level than that on the sample surface, so that the secondary electrons emanating from a pattern having a higher voltage may be reflected back to the sample side, and thus a potential contrast can be measured.

The condenser lens 238 is made of a single ceramic piece, which is processed into an axisymmetric base body 226 with a metal coating 239 applied selectively onto the surface thereof, thus forming; an upper electrode 234; a central electrode 235; and a lower electrode 236. By this design, it becomes possible to fabricate a condenser lens having a smaller diameter. In the condenser lens 238, the voltage is applied to the central electrode 235 via a lead fitting 237.

As for the objective lens 231, as similarly to the condenser lens 238, one piece of ceramic is processed into an axisymmetric shape and the metal coating is applied selectively onto the surface thereof, thereby forming an upper electrode 243, a central electrode 244 and a lower electrode 245. With this design, it becomes possible to fabricate an objective lens having a smaller diameter. In the objective lens 231, a voltage is applied to the central electrode 244 via a lead fitting 246, and upon application of this voltage, the decelerating electric field for the primary electron beam is produced between the objective lens 231 and the sample 233, as well as the lens effect provided by the objective lens 231.

If there is a region on the sample 233 to be evaluated that is relatively weak against a dielectric breakdown possibly caused by the electron beam, for example, a location in which a gate oxide film is formed, then said weak region and the other regions should be identified separately from the pattern data and stored in a pattern memory 240. Then, a signal is applied to a blanking control circuit 239 in synchronism with a scanning timing for that weak region, so that the beam may be deflected by the blanking deflector 238 so as not to pass through the blanking aperture 241 during scanning within said weak region. Thus, the beam is blocked and prevented from proceeding to the sample 233. Since such a blanking method is a technology common with the one applied to an electron beam lithography system, in which a pattern writing is performed with raster scanning being applied to a sample while successively moving the sample table (Herriott et al., EBES: *A practical Electron Lithography System*, IEEE Transactions on Electron Devices Vol.-ED-22, No. 6, July, 1975 pp 385–391), detailed description will not be given here.

Figure 4:
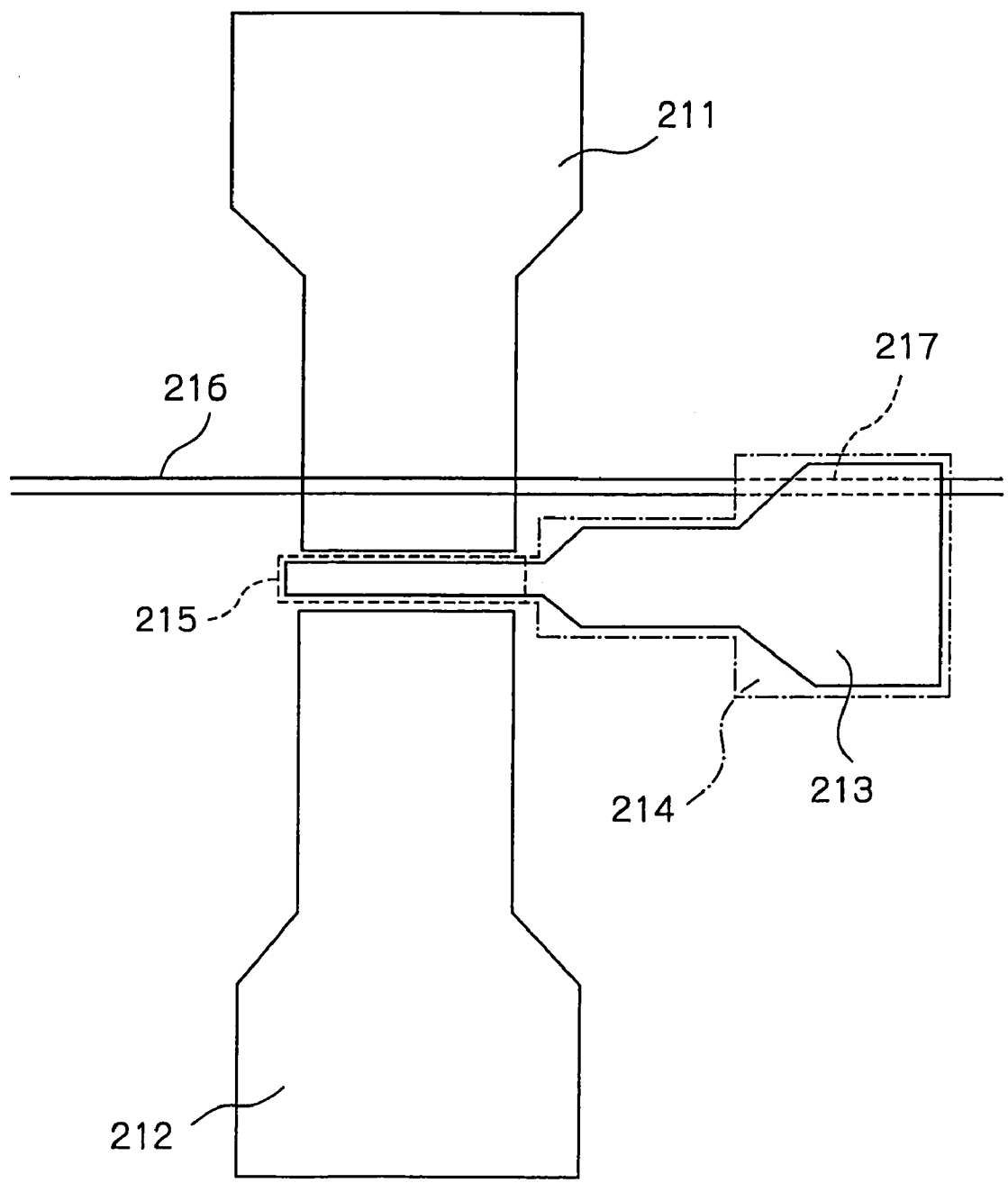
FIG. 4 is a schematic partial plan view illustrating an example for identifying a region relatively weak against a dielectric breakdown due to an electron beam irradiation.

FIG. 4 shows typical segmentation between the above-stated weak region and the other regions (i.e., robust regions). FIG. 4 is an extracted view of a MOS transistor on a TEG (Test Element Group). The MOS transistor comprises a drain 211, a source 212 and a gate 213. A region 215 surrounded by the dotted line where the gate oxide film is formed to be thinner and a region 214 of the gate 213 surrounded by the chain line, and containing therein a region connected to the gate electrode, are identified separately as regions relatively weak against the dielectric breakdown. Although the pattern of the gate 213 includes a diagonal line, the weak region has been defined by using exclusively a rectangular shape because if the diagonal line is used to define the region, data volume greatly increases.

The raster scanning is applied to the region denoted by reference numerals 216 and 217. That is, the beam has a regular intensity for the portion 216 indicated by the solid line, and the beam is blanked for the portion 217 indicated by the broken line, so as to prevent the beam from passing though that portion. Only the regions 214,215 can be scanned again with a weakened beam, or scanned again with a beam having a regular intensity but at a higher scanning rate than usual. In the case of re-scanning, the beam is blanked for the portion defined by the solid line 216.

Alternatively, a pattern of the regions 214 and 215 are stored in the pattern memory 240 in advance, and when the regions 214 and 215 are scanned, only the regions 214,215 can be scanned with a weakened beam or scanned with a beam having a regular intensity but at a higher scanning rate than usual.

In the electron beam apparatus according to the second invention, the beam is controlled in such a manner that a low dose level of electron beam or no electron beam irradiation can be applied specifically to a region relatively weak against dielectric breakdown possibly caused by the electron beam irradiation, so that the wafer can be evaluated without damaging any portions such as a gate oxide film or the like formed thereon.

In general, since said relatively weak region is small in area by ratio, even if a defect in that region were overlooked, a possibility that there is actually a defect in such a region is negligible from the viewpoint of taking all the regions into consideration. Further, if there should be no skipped evaluation without exception, the lower dose level of electron beam may be applied to the wafer for evaluation with a tolerance for undesirable S/N ratio. Alternatively, the dose level of the beam to be applied onto said weak region may be chosen to be 0, $\frac{1}{3}$, $\frac{1}{2}$ and so forth, in comparison with the normal dose level.

Embodiment of a Third Invention

Figure 5:
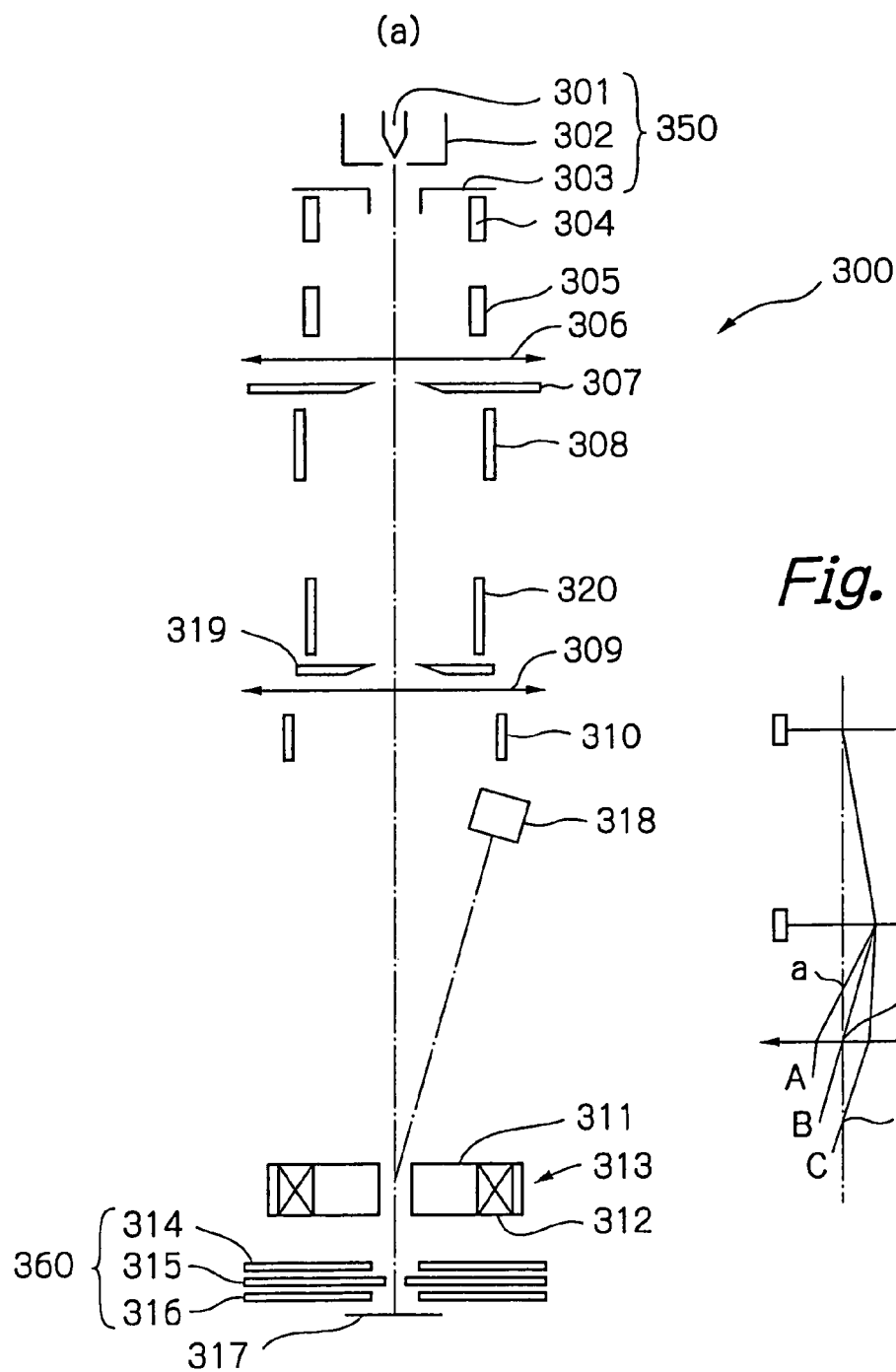
FIG. 5(*a*)is a schematic diagram of an electron beam apparatus according to an embodiment of a third invention of the present invention and FIG. 5(*b*) is a diagram illustrating a setting of a pivot point of deflection in the electron beam apparatus of FIG. 5(*a*)

A preferred embodiment of an electron beam apparatus according to the third invention will now be described with reference to FIGS. 5 and 6. Referring to FIG. 5(a), an electron beam apparatus 300 according to the third invention comprises an electron gun 350, axial aligning deflectors 304 and 305 for an axial-aligning of a primary electron beam, a condenser lens 306, an aperture 307 of square shape formed in a plate-like material, an NA aperture 319, a condenser lens 309, axial aligning deflectors 308 and 320 for axial aligning between the NA aperture 319 and the condenser lens 309, an electrostatic deflector 310 for controlling a scanning operation of the primary electron beam, an E×B separator 313 consisting of an electrostatic deflector 311 and an electromagnetic deflector 312, an objective lens 360 consisting of an upper electrode 314, a central electrode 315 and a lower electrode 316, and a secondary electron detector 318 of a detecting system functioning for detecting a detection signal for secondary electrons emanated from a sample 317.

The electron gun 350 is composed mainly of a thermionic emission cathode 301, a Wehnelt 302 and an anode 303 and functions to emit a primary electron beam so as to be irradiated against the sample 317. The thermionic emission cathode 301 is formed by polishing a mono-crystal of $LaB_6$ having a crystal orientation <100> on a surface thereof so that a diameter of a tip end portion of the crystal may be 50 $\mu$m. A flat Wehnelt having an aperture with a diameter of 1.5 mm is employed as the Wehnelt 302. Further, the anode 303 has an aperture with a diameter of 8 mm, and is disposed in a location distant from the Wehnelt 302 by 5 mm along an optical axis direction.

The primary electron beam emitted from the thermionic emission cathode 301 of the electron gun 350 is controlled by the axial aligning deflectors 304 and 305 so as to be axially aligned with an optical axis of the condenser lens 306, and irradiated against the aperture 307, where the primary electron beam is formed to have a square shaped section profile. The primary electron beam, after having passed though the aperture 307, is axially aligned by the axial aligning deflectors 308 and 320 with respect to the NA aperture 319 and the condenser lens 309, and then focused by the condenser lens 306 to form a crossover in the NA aperture 319. The primary electron beam, after having passed through the NA aperture 319, is focused by the condenser lens 309 (a reducing lens) onto the objective lens 360. The primary electron beam to be focused on the sample 317 by the condenser lens 309 is further contracted by the objective lens 360 so as to be projected and thus focused into an image on the sample 317 as the beam size of 100 nm square.

A negative voltage of –4000V is applied to the sample 317 and a negative voltage of –4100V is applied to the lower electrode 316 of the objective lens 360. This means that a voltage having a lower potential than that of the negative voltage applied to the sample 317 is applied to the lower electrode 316 of the objective lens 360. With this voltage condition, secondary electrons emanated from the higher potential pattern on the surface of the sample 317 are reflected back and only the secondary electrons emanated from the lower potential pattern are selectively allowed to pass through the objective lens 360, which make it possible to obtain a potential contrast on the sample 317 with a high S/N ratio.

Since a voltage of 20 KV is applied to the central electrode 315 of the objective lens 360, the secondary electrons emanated from the scanned points on the sample 317 are, under a normal operation, attracted and thus accelerated and focused by the high positive voltage applied to the central electrode 315 of the objective lens 360 (accelerated by an electric field produced by the objective lens 360), and the secondary electrons are then separated by the E×B separator 313 from a primary optical system and collected in the secondary electron detector 318. This E×B separator 313 comprises the electrostatic deflector 311 with eight poles, and a saddle-type deflector wound on the outside of said electrostatic deflector 311, and further a core is formed on the outside of said saddle-type deflector by a permalloy ring.

The scanning operation of the primary electron beam on the sample 317 is controlled through a two-stage deflection by the two-stage of deflector consisting of the electrostatic deflector 310 and the electrostatic deflector 311 of the E×B separator 313. Upon this operation, a pivot point of deflection of the two-stage deflectors is set in a location that may minimize the transverse chromatic aberration in the proximity of the objective lens 360. More specifically, the pivot point of deflection of the two-stage deflectors is set at a point slightly above the upper electrode 314 of the objective lens 360, thereby minimizing chromatic aberration due to deflection in the proximity of the objective lens 360. For example, as shown in FIG. 5(b), when a deflection amount of the second electrostatic deflector 311 is varied while a deflection amount of the first electrostatic deflector 310 is fixed, the trajectory for a principal ray of the electron beam changes as shown by arrows A, B and C, and, accordingly, the pivot point of deflection of the two-stage of deflectors changes as shown by points a, b and c. The location where the transverse chromatic aberration is minimum is determined by measuring a blur of the beam while varying the deflection amount of the two-stage deflectors to find an optimal point.

The detector 318 detects the condensed secondary electrons and outputs a detection result as an electric signal representing intensity thereof (a detection signal of the secondary electron) to an image forming section, though not shown. The image forming section is additionally supplied with a scanning signal applied to the electrostatic deflector 310 and the electrostatic deflector 311 for deflecting the primary electron beam. The image forming section can synthesize the scanning signal and the electric signal to form image data, thus to make up and/or display an image (SEM image) representing a scanned surface of the sample 317. This image data may be compared with reference data for an indefectible sample so as to detect any defects in the sample 317.

Since a plurality of electrodes of the E×B separator 313 is formed by processing a machine-processable ceramic and thereafter applying a metal coating selectively to the surface thereof, an outer diameter of the E×B separator 313 can be made smaller. In addition, since the electromagnetic deflector 312 is a saddle-type deflector, the outer diameter thereof can also be made smaller. Owing to these facts, the E×B separator 313 can have an outer diameter of about 40 mm, thereby contributing to an increase of the throughput. That is, for example, if a total of twelve sets of electron optical column is disposed over a sheet of sample 317, a throughput increased by 12 times can be obtained.

Further, by minimizing the transverse chromatic aberration through a optimum pivot point of deflection in the proximity of the objective lens 360 as described above, the beam current of 20 nA or higher is obtainable with a beam diameter of 110 nm. This will be explained more specifically. FIG. 6 shows a graphic chart for calculating the beam current to be obtained in the above-described optical system when a pivot point of deflection by the two-stage deflectors is set in a location that minimize transverse chromatic aberration in the proximity of the objective lens 360, and a distance between the lower electrode 316 of the objective lens 360 and the sample 317 is assumed to be 2 mm in the optical axis direction. More specifically, a bore diameter of the upper electrode 314, the central electrode 315 and the lower electrode 316 is 4 mm, 2 mm and 3 mm, respectively, each space between these three electrodes is 2 mm, and a thickness each of these electrodes is 2 mm.

Figure 6:
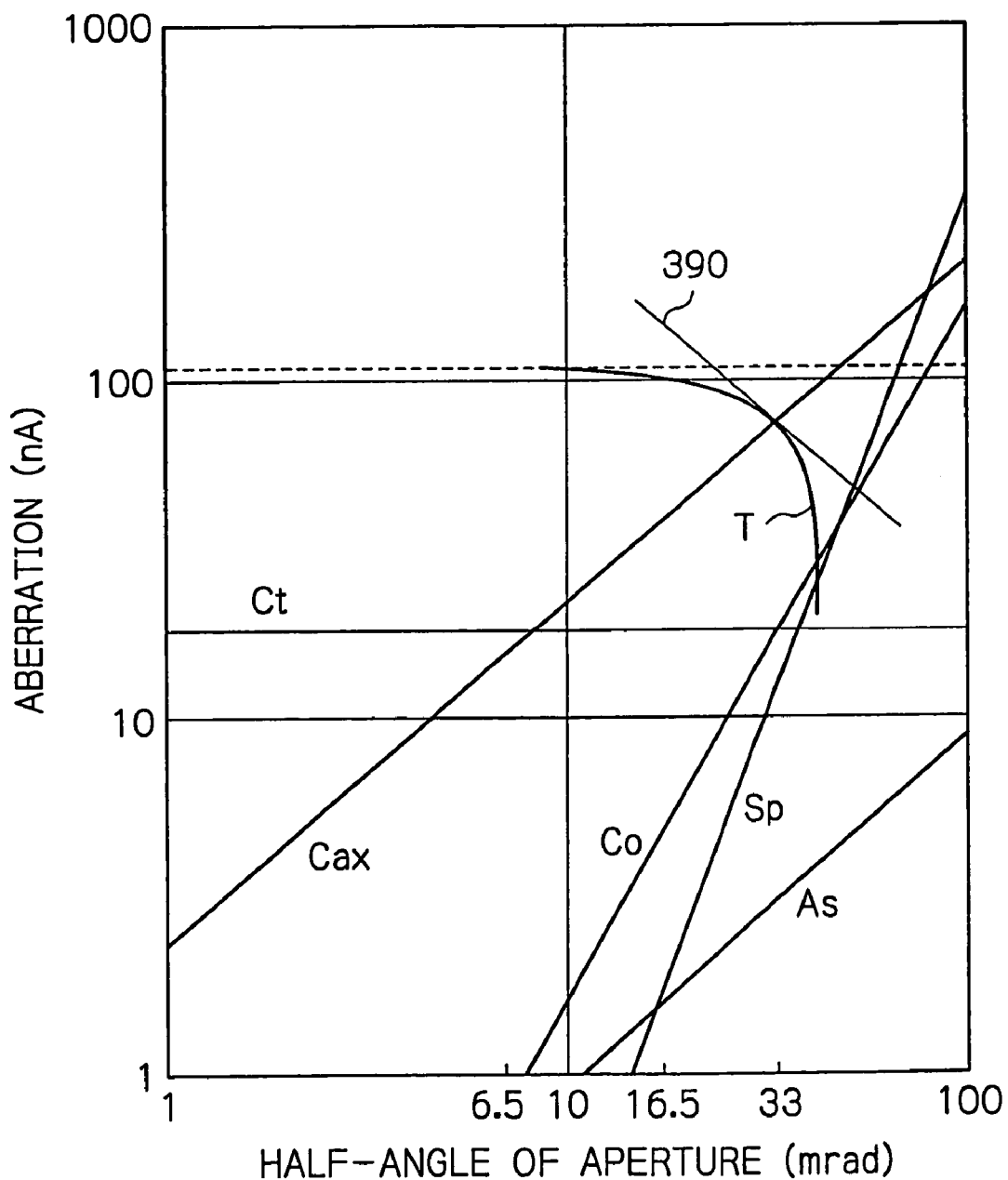
FIG. 6 is a graphic chart indicating a calculation result of a beam current to be obtained in an optical system in the embodiment of FIG. 5.

A deflection point of the two-stage deflectors 310 and 311 is set substantially at a position of lower surface of the upper electrode 314 and an object point is set at 100 mm above the upper surface of the central electrode 315. In FIG. 6, "Ct" designates transverse chromatic aberration, "Cax" designates axial chromatic aberration, "Co" designates coma aberration, "Sp" designates spherical aberration and "As" designates astigmatic aberration. Further, "T" denotes a diameter of a beam without any aberration measured on the sample 317 upon obtaining a beam diameter of 110 nm, and T may be determined from the expression:

$$T^2 = 110^2 - Ct^2 - Cax^2 - Co^2 - Sp^2 - As^2,$$

which will be shown as a curve in FIG. 6. Reference numeral 390 designates a straight line inclined down in the rightward direction at an angle of 45°, and a contact point of this straight line 390 with the curve T may be defined to show an optimal value, i.e. a condition where a maximum beam current is obtained with the beam diameter of 110 nm. That is, the half-angle of aperture=33 mrad, Topt=76.4 nm, and the beam current I may be expressed as:

$$I = \pi \alpha^2 B \cdot \pi (d/2)^2$$
$$= \pi^2 (33 \times 10^{-3})^2 \times (76.4 \times 10^{-5}/2)^2 \times 1.5 \times 10^5$$
$$= (\pi \times 1.26 \times 10^{-5} \times 1 \times 10^{-2})^2 \times 1.5 \times 10^5$$
$$= 23.5 \text{ nA,}$$

(where, α: the half-angle of aperture, d: Topt, B: brightness) indicating that a beam current equal to or more than 20 nA can be obtained. It is to be appreciated that the above result comes from a calculation where the crossover image has been contracted to be a probe, and a higher beam current may be obtained for the case where a contracted image of the electron beam having passed though the aperture is used as the probe.

Further, the electron gun 350 may be activated with a space charge limited condition. In this case, assuming the yield (transmittance) of the secondary electron to be 50% similarly to that with the TFE electron gun, the shot noise, $I_N$, is expressed as:

$$I_N = \Gamma \times (2eI\Delta f)^{1/2} \text{(where, } \Gamma = 0.13 \text{ and } I = 20 \times 0.5 \times 10^{-9} =$$
$$10 \times 10^{-9})$$
$$= 0.13 \times (2 \times 1.6 \times 10^{-19} \times 10 \times 10^{-9} \times 100 \times 10^6)^{1/2}$$
$$= 7.35 \times 10^{-11} A$$

and accordingly, the S/N will be expressed as:

$$S/N = 10 \times 10^{-9} / 7.35 \times 10^{-11} = 136,$$

meaning that the shot noise can be reduced so as to satisfy the condition of S/N>45, which is required to perform defect inspection or the like; and there is no need to repeat the scanning, e.g. two or four times, and then to apply the averaging and adding operation as is the case in the prior art. However, but a sufficient signal can be obtained with one-time scanning in the operation at a frequency level of 100 MHz or higher, and a beam can be obtained that enables a resolution of 100 nm with the condition of S/N>45.

According to a first aspect of the third invention as described above, since an innovative electron beam apparatus has been provided, in which an electron beam emitted from the electron gun having a hot cathode is irradiated against the aperture and the electron beam after having passed through said aperture is contracted and projected onto the sample, and secondary electrons emanated from the sample are accelerated by the electric field produced by the objective lens and guided by the E×B separator into the secondary electron detector, wherein when the two-stage of deflectors is operated to scan the sample, the pivot point of deflection by said two-stage of deflectors is set in such a location that may minimize a transverse chromatic aberration due to the optimum deflection pivot in the proximity of said objective lens, therefore the beam diameter will not become larger even after the beam has been deflected. Further, since the contracted image of the aperture is used as the beam, a higher beam current can be obtained.

According to another aspect of third invention, since in the first aspect of the third invention as described above, said electron gun is adapted to be operative under the space charge limited condition, a shot noise can be reduced so as to satisfy the condition of S/N>45, which is required to perform defect inspection or the like, and there is no need for applying the averaging and adding operation. Rather, a sufficient signal can be obtained with one-time scanning, and a beam can be obtained that enables a resolution of 100 nm with the condition of S/N>45.

According to a third aspect of the third invention, since in the first aspect of the third invention as described above, said aperture is square shaped, therefore a higher beam current can be obtained with a lower brightness.

According to a fourth aspect of the third invention, since in the first aspect of the third invention as described above, a negative voltage is applied to the sample and a voltage having a lower potential than that of said sample is applied to the lower electrode of the objective lens, therefore a voltage contrast on the sample can be obtained with a preferable S/N ratio.

Embodiment of a Fourth Invention

Figure 7:
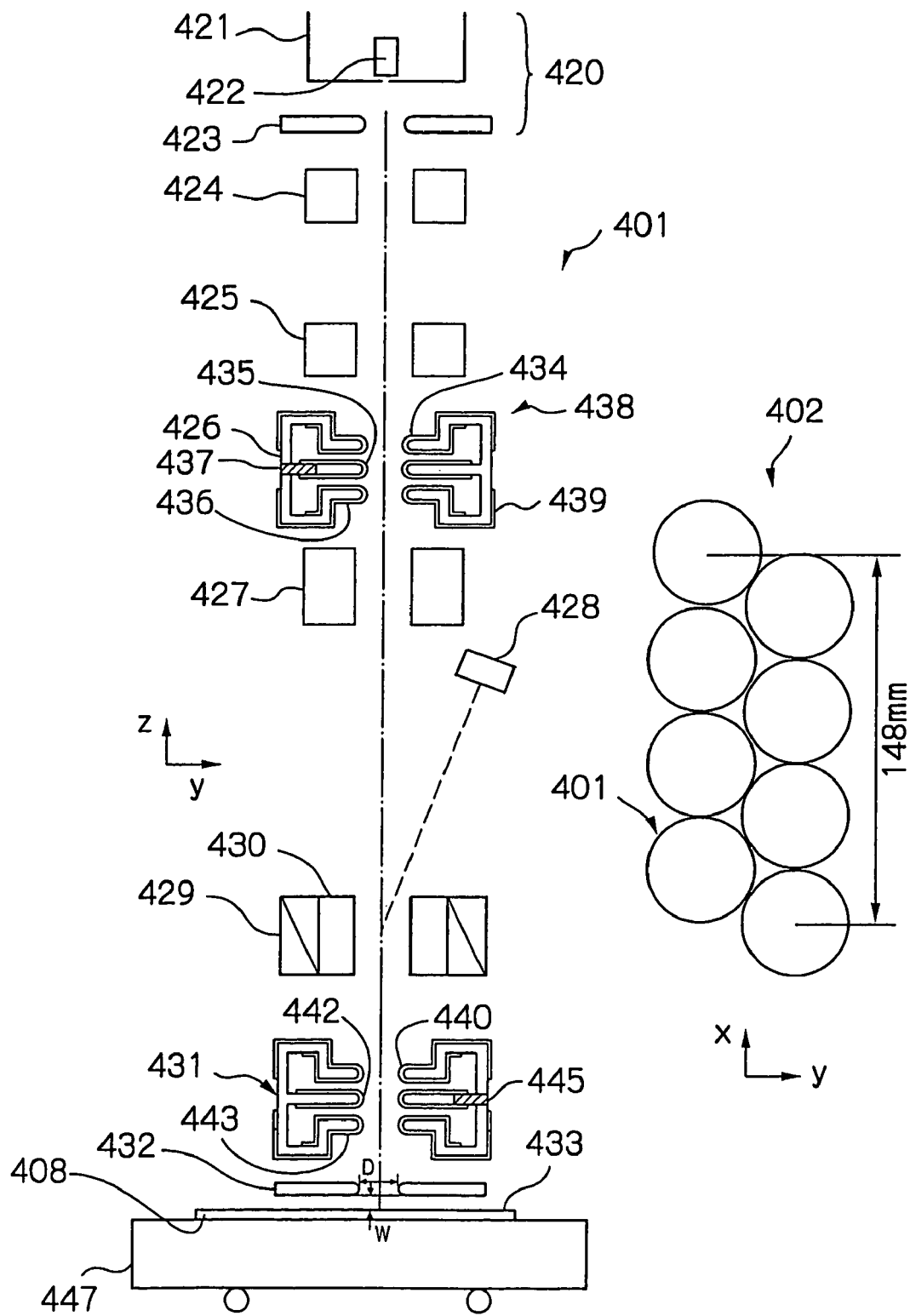
FIG. 7 is a side sectional view and a top view illustrating a schematic configuration of an electron beam apparatus according to an embodiment of a fourth invention of the present invention.

FIG. 7 shows a side sectional view and a top view, respectively, of an electron beam apparatus according to an embodiment of a fourth invention.

As shown in the top view of FIG. 7, the electron beam apparatus according to the present embodiment comprises a plurality of similarly configured optical column 402 (eight optical columns in the example shown in FIG. 7) arranged in parallel with one another above a wafer 408. One optical column 401 among those optical columns 402 comprises, as shown in the side sectional view of FIG. 7, a three-electrode type electron gun 420 comprising a Wehnelt 421, a cathode 422 and an anode 423, for emitting a primary electron beam; axial aligning electrostatic deflectors 424, 425 for aligning an axis of the primary electron beam with respect to a subsequent lens; a condenser lens 438; an electrostatic deflector 427; an E×B separator (429, 430); an objective lens 431; an axisymmetric electrode 432; and a detector 428 for detecting a secondary electron beam emanated from the wafer 408. The wafer 408 is mounted on a stage 447 for transferring the wafer 408 within an X-Y plane. By way of this, secondary electron images of the wafer 408 for an overall region to be inspected can be obtained.

In each of the optical columns, the primary electron beam emitted from the electron gun 420 is once focused by the condenser lens 438 into a crossover image in the electron gun side of the E×B separator (429, 430) and further focused through the objective lens 431 onto the sample surface 433. During this process, the electrostatic deflector 427 and the electromagnetic deflector 429 cooperate to make the primary beam scan the sample surface 433. The secondary electron beam emanated from a scanned point of the wafer is accelerated by the objective lens 431, and the secondary electron beam, after having passed through said lens 431, is deflected by the E×B separator (429, 430) toward the direction indicated by the dotted line in the drawing to be detected by the detector 428. An output signal from the detector 428 is sent to an image processing section, though not shown in the drawing, where the secondary electron image of the sample surface 433 is generated.

The axisymmetric electrode 432 disposed between the objective lens 431 and the wafer 408 functions to provide a voltage lower than a voltage on the sample surface, thereby partially decreasing an axial potential to a lower level than that on the sample surface, so that the secondary electrons emanated from a pattern having a higher voltage may be reflected back to the sample side, and thus a voltage contrast can be improved. This will be explained later. To obtain a topology image or an image representing a difference in the material, a higher voltage than the wafer 408 may be applied to the axisymmetric electrode 432 so as to increase a detecting yield of the secondary electron.

The condenser lens 438 is made of a single ceramic piece, which is processed into an axisymmetric base body 426 with a metal coating 439 applied selectively onto the surface thereof, thus forming an upper electrode 434, a central electrode 435 and a lower electrode 436. With this design, it becomes possible to fabricate such a condenser lens having a smaller diameter. In the condenser lens 438, a voltage is applied to the central electrode 435 via a lead fitting 437.

As for the objective lens 431, similar to the condenser lens 438, a single ceramic piece is processed into an axisymmetric shape, and the metal coating is applied selectively onto the surface thereof, thereby forming an upper electrode 440, a central electrode 442 and a lower electrode 443. With this design, it becomes possible to fabricate an objective lens having a smaller diameter. In the objective lens 431, a voltage is applied to the central electrode 442 via a lead fitting 445, and upon this voltage application, a decelerating electric field for the primary electron beam is produced between the objective lens 431 and the wafer 408, as well as the lens effect provided by the objective lens 431.

Thus in this embodiment, since it has become possible to use the electrodes having a smaller diameter for the condenser lens 438 and the objective lens 431, which allows an overall outer diameter of the optical column 401 to be made much smaller, therefore it is possible to install a plurality of optical columns arranged in parallel with one another, as shown in FIG. 7. Since in respective optical columns, different secondary electron images corresponding to different regions of the wafer 408 can be obtained, throughput of the wafer evaluation may be improved in proportion to the number of employed optical columns.

Figure 8:
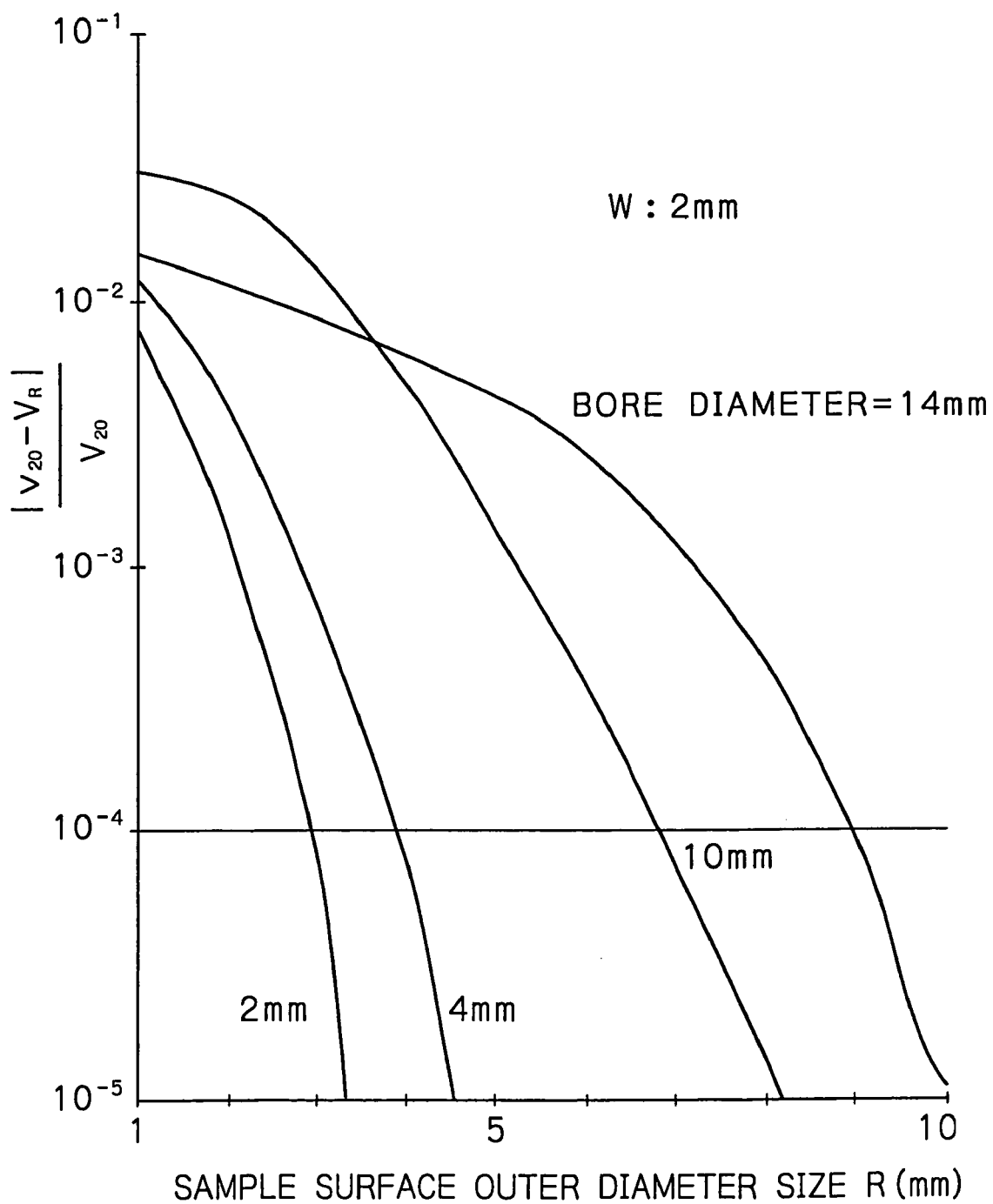
FIG. 8 is a diagram illustrating a simulation result obtained by evaluating an effect of outer diameter of a wafer sample in order to demonstrate a principle of the fourth invention.

FIG. 8 is a diagram illustrating a result of simulation by calculating a voltage to be applied to the central electrode which can satisfy a focusing condition of the objective lens, as a function of the outer diameters of the wafer sample, by using a parameter W representing a working distance of the objective lens 431 and another parameter D representing a bore diameter of the lower electrode 432 of said objective lens 431 disposed most proximal to the wafer. In this context, the working distance of the objective lens 431, W, is meant to be a distance between the sample surface 433 and the under surface of the lower electrode 432 of the objective lens 431 disposed most proximal to the wafer.

As shown in FIG. 8, assuming that a voltage to be applied to the central electrode 442, which can satisfy the focusing condition for the sample surface with a sufficiently large outer diameter, is denoted as $V_{20}$ and a voltage to be applied to the central electrode, which can satisfy the focusing condition for the sample surface with an outer diameter of R mm, is denoted as $V_R$, then the Y-axis indicates a value representing a difference between those two values which has been normalized by $V_{20}$, i.e., $|V_{20}-V_R|/V_{20}$.

Variation in focusing condition means that the axial potential distribution is varied due to the effect depending on a different outer diameter of the sample surface. It has been judged that if the value for $|V_{20}-V_R|/V_{20}$ is not greater than $10^{-4}$, the effect from the outer diameter of the sample surface is negligible.

As can be seen from FIG. 8, under the given condition of W=2 mm, the voltage difference representing the focusing condition falls into a range not greater than $10^{-4}$ with the sample surface outer diameter size R equal to or greater than 9 mm for the bore diameter of 14 mm; with the R equal to or greater than 7 mm for the bore diameter of 10 mm; with the R equal to or greater than 4 mm for the bore diameter of 4 mm; and with the R equal to or greater than 3 mm for the bore diameter of 2 mm. Accordingly, if "(the working distance W)+(half of the bore diameter D/2)≦R", then it is determined that there would be substantially no effect from the outer diameter of the sample surface.

From the above result, it is considered that, in order to evaluate the region on the wafer 408 defined as the inner side with respect to the peripheral edge of the wafer 408 by a distance not smaller than R mm, if the axisymmetric objective lens 31 is fabricated so as to satisfy the condition:

$$W+D/2 \leq R$$

expression (1), then the region of the sample surface 433 subject to the inspection, which is defined as the inner side with respect to the wafer peripheral edge by a distance not smaller than R mm, may be appropriately evaluated yet with avoiding substantially any effects by the peripheral edge of the wafer 408.

As for the region requiring an evaluation in an 8" (inch) wafer or a 12" (inch) wafer, it is not necessary to evaluate such a region that is distant from the wafer edge by an amount not greater than 5 mm even in the case of fabricating 5 mm square chips. Typically, chips greater than 5 mm square are fabricated in most cases, and therefore even if the evaluation could be successfully applied only to a region distant from the wafer peripheral edge by a distance of not less than 5 mm, it would be considered sufficient. Accordingly, in that case, the above expression (1) may be;

$$W+D/2 \leq 5 \text{ mm}$$

expression (2)

The electron beam apparatus according to this embodiment evaluates the wafer 408 based on the obtained secondary electron image in a manner, for example, as described below.

In a pattern defect inspecting method by way of the pattern matching applied to the wafer 408, a control section (not shown) controls the electron beam apparatus, compares a secondary electron beam reference image for the wafer, which has no defect and has been stored in a memory in advance, to an actually detected secondary electron beam image and then calculates a similarity between them. For example, if the similarity falls below a threshold value, then it is determined that "a defect exists", and a similarity exceeding the threshold value is determined as "no defect". At this stage, the detected image can be indicated in a display, though not shown. This will allow an operator to confirm and evaluate ultimately whether or not the wafer 408 actually has a defect. Further, images for partial regions may be compared for matching to one another, so that the particular region including a defective pattern may be automatically detected.

Further, for such a wafer that includes a plurality of the same dies, by comparing detected images of the dies to one another, a defective portion can be detected without the need for using the reference image as in the case above. For example, if it is determined that a first detected die image is not similar to a second detected die image, and a third detected die image is the same or similar to the first detected die image, then it may be determined that the second detected die image does have a defect. If a further precise algorithm for the comparative matching is used, it may become possible to detect the defective portion defined in the second detected die image.

Further, the electron beam apparatus according to this embodiment can also be used as a line width measuring apparatus for measuring a line width of a pattern formed on a wafer. A width of a part where an actual intensity signal of a secondary electron obtained by scanning an actual pattern on the wafer in a specific direction continuously exceeds a threshold level, which has been determined in advance through calibration, can be measured as the line width of that specific pattern. If the thus measured line width falls out of the predetermined range, then it may be determined that said pattern does have a defect.

The above line width measuring method can be applied to measurement of an aligning accuracy between respective layers of a wafer 408 containing a plurality of layers. For example, a second aligning pattern to be formed by the lithography applied to a second layer should be formed in advance in the proximity of a first aligning pattern to be formed by the lithography applied to a first layer. Said line width measuring method is used to measure a pattern interval between those two patterns, and then the measured value is compared with a design value so as to determine aligning accuracy between those two layers. It is a matter of course that this method may be applied to a wafer containing three or more layers. In that case, if the interval between the first and the second aligning patterns is set to be approximately equal to a beam interval between any adjacent beams of a plurality of primary electron beams, accuracy can be measured with a minimum scanning amount.

Further, the electron beam apparatus according to this embodiment may be used as an apparatus for measuring a voltage contrast between patterns formed on the wafer 408. For example, it is assumed that if a potential of −10V had been applied to the axisymmetric electrode 432 with respect to a wafer potential of 0V, those two patterns formed on the wafer have potentials of −4V and 0V, respectively. In that case, since the secondary electron emanated from the lower potential pattern has an upward speed corresponding to a kinetic energy of 2 eV on the equipotential surface of −2V, therefore the secondary electron can run over the potential barrier and escape from the axisymmetric electrode 432, which will be detected by the detector. On the other hand, the secondary electron emanated from the higher potential pattern cannot overcome the potential barrier of −2V but is pushed back toward the wafer surface, which would not be detected. Accordingly, the detected image of the lower potential pattern is brighter, while the detected image of the higher potential pattern is darker. Thus, the voltage contrast for the region to be inspected on the wafer 408 can be accomplished. If the brightness and the potential for the detected image had been calibrated in advance, the potential of the pattern may be measured from the detected image. Also from the potential distribution, a defective portion of the pattern can be evaluated.

If a blanking deflector is arranged in the electron beam apparatus of this embodiment so as to deflect the primary electron beam to a stopper (not shown) disposed in the vicinity of the crossover focused point at a predetermined cycle and thereby to permit said beam to pass through for a short period and to block it for the rest of the period, which will be repeated, then it will be possible to form a bundle of beams having a short pulse width. If such a beam having a short pulse width is used to measure the potential on the wafer as described above, the device operation can be analyzed with high time resolution. That is, the electron beam apparatus of the present invention can be used as what is called an EB tester.

The preferred embodiments of the fourth invention have been described as above, but the fourth invention is not limited only to the above-discussed examples.

For example, although the objective lens working distance and the bore diameter have been denoted W and D, respectively, and the values relating to the lower electrode 432 disposed most proximal to the wafer have been used in the above embodiments, for a case where this lower electrode has not been provided or not been operative, the objective lens working distance W and the bore diameter D may be determined with respect to the electrode 443 of the objective lens 431.

Further, although in the above examples, the semiconductor device has been used as the sample to be inspected, the fourth invention is not limited to this, but an arbitrary sample including, for example, a mask having a pattern formed thereon, for which a defect may be detected by using the electron beam, may be an object to be evaluated.

Further, a configuration of the electron beam apparatus may be modified as desired, and the small-diameter lenses may be used in the apparatus without being limited to the condenser lens or the objective lens.

Further, as far as the pattern of the wafer 408 can be inspected, a charged particle beam other than the electron beam may be used.

As has been described above in detail, according to the electron beam apparatus of the fourth invention, for such an electron beam apparatus that uses an objective lens of a decelerating electric field type that can reduce an axial chromatic aberration coefficient and a spherical aberration, advantageously a design scheme of the objective lens aiming for a highly accurate evaluation of a sample by eliminating substantially any effect from a peripheral edge of the sample has been obtained.

Further, according to one aspect of the fourth invention, since at least objective lens has been designed to have such an electrode that is made of insulating material formed into an axisymmetric structure with a metal coating applied selectively onto a surface thereof, advantageously a lens diameter may be successfully reduced.

Further, according to another aspect of the fourth invention, since a plurality of electron optical systems has been installed above a single sheet of wafer, advantageously a throughput of the sample evaluation may be improved.

Embodiment of a Fifth Invention

Figure 9:
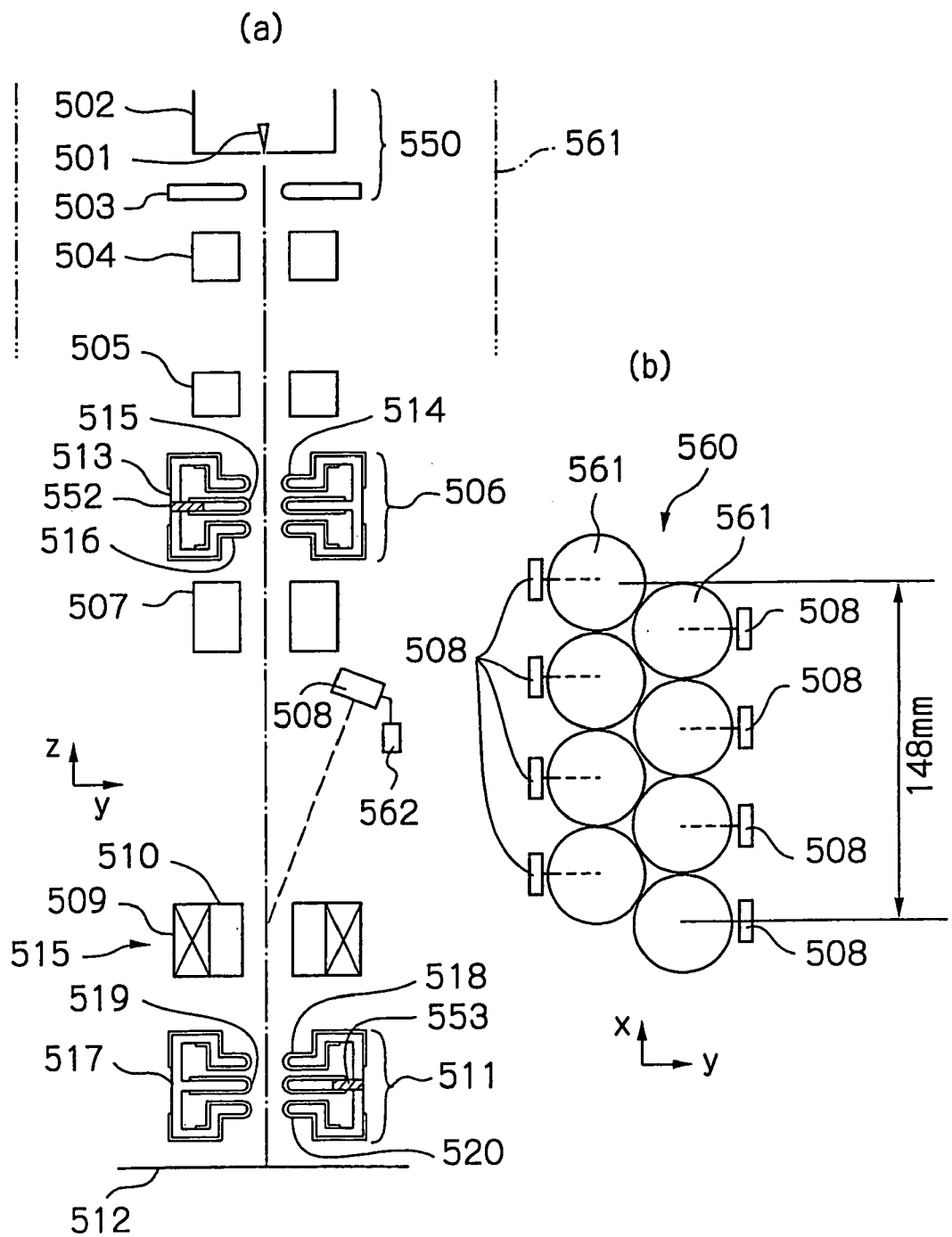
FIG. 9 is a schematic diagram of an electron beam apparatus according to an embodiment of a fifth invention of the present invention.

FIG. 9 is a schematic diagram showing an embodiment implementing an electron beam apparatus according to a fifth invention. As shown in FIG. 9, the electron beam apparatus comprises a plurality of similarly configured electron optical columns 560 (eight optical columns in the illustrated example) arranged in parallel with one another above a sample 512. One electron optical column 561 among those optical columns comprises an electron gun 550, axial aligning deflectors 504, 505 functioning for axial aligning of a primary electron beam, a condenser lens 506, an electrostatic deflector 507 for controlling a scanning operation of the primary electron beam, an E×B separator 551 consisting of an electromagnetic deflector 509 and an electrostatic deflector 510, an objective lens 511, and a detector 508 for detecting a detection signal of either one of secondary electrons, back scattered electrons or absorbed electrons, which have emanated from the sample 512.

The electron gun 550 comprises a Wehnelt 502, a thermionic emission cathode 501 and an anode 503, and functions for emitting a primary electron beam so as to be irradiated onto the sample 512. The thermionic emission cathode 501 is made of a mono-crystal of LaB6. The primary electron beam emitted from the thermionic emission cathode 501 of the electron gun 550 is axially aligned by the axial aligning deflectors 504 and 505 with respect to the condenser lens 506, which then focuses the primary electron beam onto the sample 512. The primary electron beam, after having been focused by the condenser lens 506, is then formed into an image on the sample 512 by the objective lens 511. At the same time with this step, the electrostatic deflector 507 and the electromagnetic deflector 509 of the E×B separator 551 cooperate to deflect the primary beam so as to scan the surface of the sample 512. Since the angle of deflection by the electromagnetic deflector 509 has been set approximately twice as much as the angle of deflection by the electrostatic deflector 507, therefore there will be little transverse chromatic aberration.

Either one of the secondary electrons, back scattered electrons or absorbed electrons emanated from a scanned point on the sample 512 is attracted by a high positive voltage applied to a central electrode 519 of the objective lens 511 and thereby accelerated and focused, and subsequently separated from a primary optical system by the E×B separator 551 and introduced into a secondary optical system thus to be focused on the detector 508.

The detector 508 detects either one of the focused secondary electrons, back scattered electrons or absorbed electrons, and then sends an electric signal representing the intensity thereof (a detection signal for either one of the secondary electrons, back scattered electrons or absorbed electrons) to an image forming section, though not shown in the drawing. The image forming section is further supplied with a scanning signal which has been given to the electrostatic deflector 507 and the electromagnetic deflector 509 for deflecting the primary electron beam. The image forming section can synthesize the scanning signal and the electric signal to make the image data so that the image (SEM image) representing the scanned surface area of the sample 512 may be formed or displayed. The image data is compared with reference image data representing a normal sample without any defects thus to detect any defective portion of the sample 512.

Further, as shown in FIG. 9, the condenser lens 506 is a lens made of a single ceramic piece as an insulating material, which has been processed to include a plurality of electrodes with a metal coating applied selectively to a surface thereof. The plurality of electrodes of the condenser lens 506 consists of an upper electrode 514, a central electrode 515 and a lower electrode 516, and a voltage is applied to the condenser lens 506 via a lead fitting 552. Further, the objective lens 511 is, similar to the condenser lens 506, a lens made of single ceramic piece as an insulating material, which has been processed to include a plurality of electrodes with a metal coating applied selectively to a surface thereof. The plurality of electrodes of the objective lens 511 consists of an upper electrode 518, a central electrode 519 and a lower electrode 520, and a voltage is applied to the objective lens 511 via a lead fitting 553. As discussed above, the condenser lens 506 and the objective lens 511 can be processed as lenses with smaller outer diameters and thus the electron optical column 561 can be fabricated with a smaller outer diameter, whereby a large number of electron optical columns 561 may be accommodated in side-by-side arrangement over a sheet of sample 512.

A feature of the fifth invention will now be described. A heating electric power of said thermionic emission cathode 501 is adjusted by means of a current to be applied to graphite (not shown) compressed against both sides of the cathode 501. In a coarse tuning of the heating electric power of the thermionic emission cathode 501, as practiced in the prior art, the heating electric power is set such that a lower increasing rate of the emission current of the electron gun 550 may be accomplished during the period when the heating electric power of the thermionic emission cathode 501 is increased. Then, after the axial alignment having been applied to the primary electron beam with respect to the lens by the axial aligning deflectors 504 and 505 and the electrostatic deflector 507, the primary electron beam is irradiated against the sample 512, as described above, so as to scan the surface of the sample 512 by superposing the scanning voltage and the scanning current onto the electrostatic deflector 507 and the electromagnetic deflector 509 of the E×B separator 551. Then, a secondary electron signal (a detection signal) obtained at a time of line scanning on the sample 512 such as a flat sample of bare silicon or the like is indicated on the CRT (cathode-ray tube), while an effective value for the shot noise is measured by a noise meter 562. The noise meter 562 has been designed with such a configuration, in which the secondary electric signal is passed though a band-pass filter, and the noise current included in that band is commutated and smoothed so as to cause a wave in the meter to indicate the effective value.

Subsequently, a certain level of beam current is applied to the thermionic emission cathode 501, and the signal/noise ratio (the S/N ratio) or the noise level measured in the detector 508 during the period when the primary electron beam is irradiated against the sample 512 while changing the heating electric power of the thermionic emission cathode, is evaluated thus to determine a value for the heating electric power of the thermionic emission cathode 501.

Figure 10:
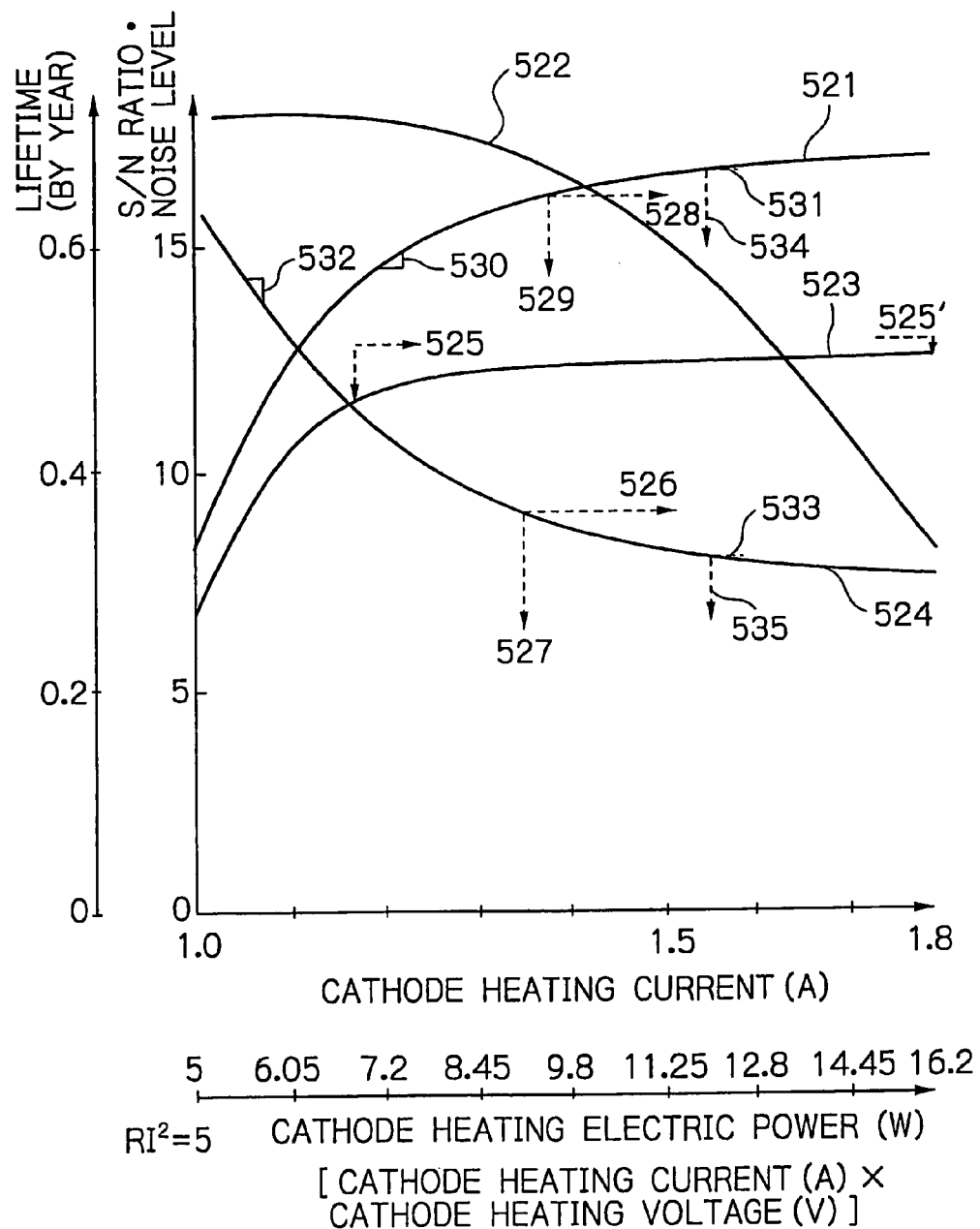
FIG. 10 is a graphic chart indicating measured values for a S/N ratio and a noise level in the embodiment shown in FIG. 9.

FIG. 10 shows the measured values of the signal/noise ratio (the S/N ratio) and the noise level measured in the detector 508 during a period when the primary electron beam is irradiated against the sample 512 while changing the heating electric power of the thermionic emission cathode 501. In FIG. 10, a curve designated by reference numeral 521 represents the S/N ratio when a certain level of beam current is applied to the thermionic emission cathode 501. A curve designated by reference numeral 522 represents a lifetime of the thermionic emission cathode 501, which has been estimated from a relationship between the electric power and the temperature in the thermionic emission cathode 501. A curve designated by reference numeral 523 represents an emission current of the electron gun 550. A curve designated by reference numeral 524 represents the noise level measured when a certain level of beam current is applied to the thermionic emission cathode 501. It is to be noted that in the coarse tuning, the heating electric power of the thermionic emission cathode 501 is set within a range in which the electron gun current of the electron gun 550 is saturated (the range defined by and between reference numerals 525 and 525').

As can be seen from FIG. 10, as the heating electric power of the thermionic emission cathode 501 is increased, that is, as the temperature of the thermionic emission cathode 501 is increased, the shot noise (the noise level resultant from a statistical variation in the number of electron) is decreased, thereby increasing the S/N ratio. Accordingly, by evaluating the signal/noise ratio (the S/N ratio) or the noise level measured in the detector 508 during a period when a certain level of beam current is applied to the sample from the current emitted from the thermionic emission cathode 501 and the primary electron beam is irradiated against the sample 512 while changing the heating electric power of the thermionic emission cathode 501 and thereby determining the value for the heating electric power of the thermionic emission cathode 501, the shot noise can be reduced and the S/N ratio can be increased and thereby the secondary electrons or the like emanated from the sample can be detected with an improved S/N ratio. Further, since the temperature of the thermionic emission cathode 501 can be controlled so as not to reach an undesirable high temperature, the operating lifetime of the thermionic emission cathode 501 can be extended. In addition, by tentatively setting the cathode temperature easily under the condition by the prior art where the emission current is saturated, a condition accomplishing a higher S/N ratio can be established in a relatively short time to facilitate easy setting of the optimal cathode heating electric power. Furthermore, by applying firstly the coarse tuning of the heating electric power of the thermionic emission cathode 501 and secondly the fine tuning of the heating electric power of the thermionic emission cathode 501 according to the method of the present invention described above, an optimal cathode heating condition can be established in a short time.

Alternatively, the value for the heating electric power of the thermionic emission cathode 501 can be determined in such a manner that the S/N ratio may exceed a predetermined value or the noise level may fall onto or below a predetermined value when a certain level of beam current is applied to the sample from the electron flow emitted from the thermionic emission cathode 501. For example, the value for the heating electric power of the thermionic emission cathode 501 (the heating current of the cathode×the cathode heating voltage) may be determined to be a value designated by reference numeral 529 such that the S/N ratio can exceed the value designated by reference numeral 528 in FIG. 10. Alternatively, the value for the heating electric power of the thermionic emission cathode 501 may be determined to be a value designated by reference numeral 527 such that the noise level is not greater than a value designated by reference numeral 526.

Alternatively, the value for the heating electric power of the thermionic emission cathode 501 may be determined in such a manner that the increasing rate of the S/N ratio to the heating electric power can fall onto or below a predetermined value or the decreasing rate of the noise level can fall onto or below a predetermined value when a certain level of beam current is applied to the sample from the beam emitted from the thermionic emission cathode 501. For example, the value for the heating electric power of the thermionic emission cathode 501 may be determined to be a value designated by reference numeral 534 such that the increasing rate of the SIN ratio to the heating electric power defined by reference numeral 530 or 531 can be within the range of increasing rate defined by reference numeral 531 in FIG. 10. Alternatively, the value for the heating electric power of the thermionic emission cathode 501 may be determined to be a value designated by reference numeral 535 such that the decreasing rate of the noise level as designated by reference numeral 532 or 533 can fall within a range of decreasing rate defined by reference numeral 533.

In an alternative way, the value for the heating electric power of the thermionic emission cathode 501 may be determined by evaluating the noise current/beam current ratio. That is, the value for the heating electric power of the thermionic emission cathode 501 may be determined such that the value defined by normalizing the noise current by the beam current may not be greater than a predetermined value.

According to the fifth invention, since such an innovative electron optical column has been provided, which is configured such that the electron beam emitted from the thermionic emission cathode is irradiated onto the sample and either one of the secondary electrons, the back scattered electrons or the absorbed electrons, which has been emanated from the sample, is focused onto the detecting system, wherein the value for the heating electric power of the thermionic emission cathode is determined based on the evaluation of the signal/noise ratio or the noise level measured in the detecting system during the period when the electron beam is irradiated onto the sample while changing the heating electric power of the thermionic emission cathode, therefore the shot noise is decreased and the S/N ratio is increases, so that the secondary electron or the like emanated from the sample can be detected with an improved S/N ratio.

Embodiment of a Sixth Invention

The present embodiment uses an electron beam apparatus as described in the preceding embodiments to be applied to an evaluation of a wafer in a semiconductor device manufacturing process.

Figure 11:
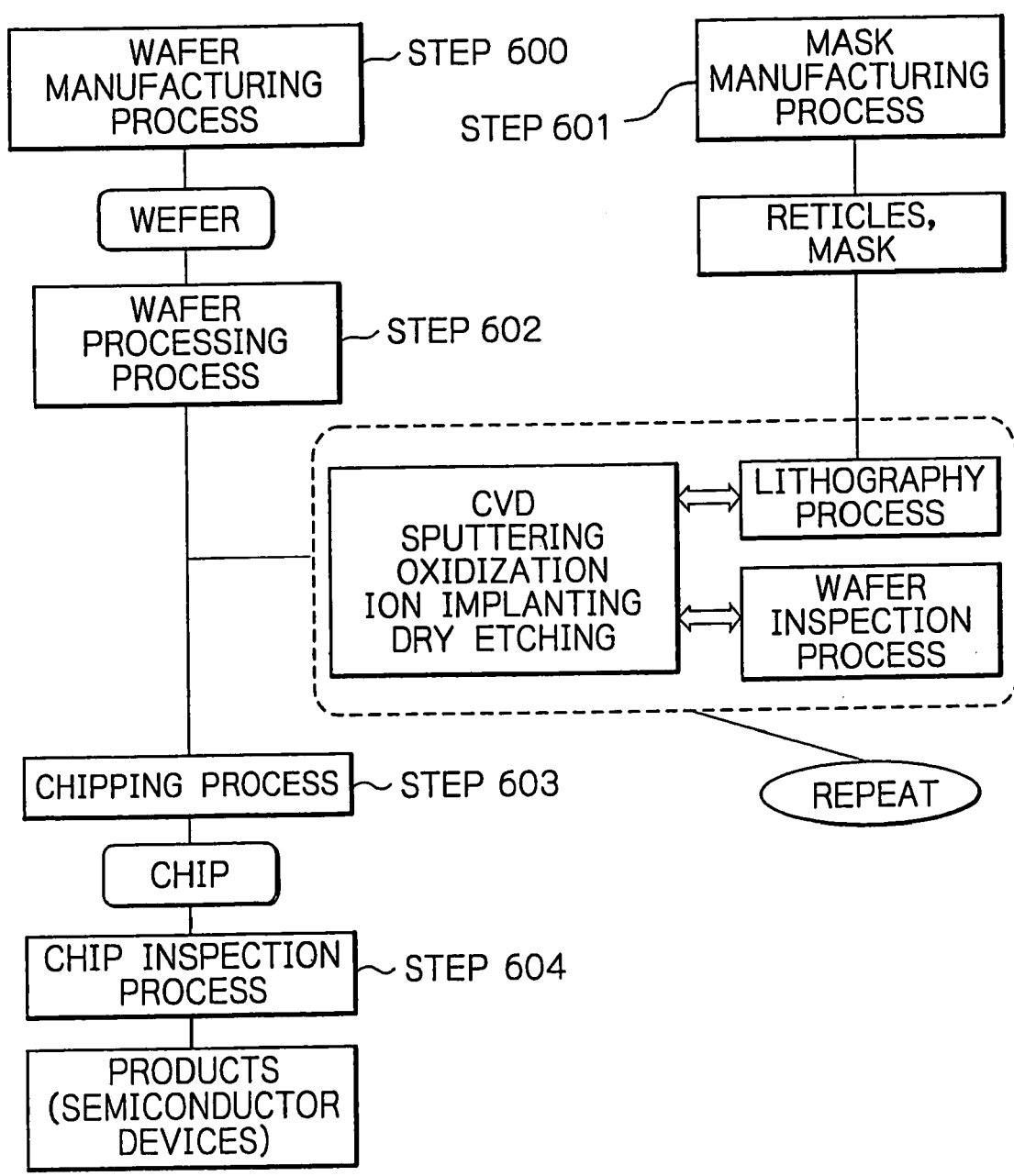
FIG. 11 is a flow chart showing a series of semiconductor device manufacturing processes according to a sixth invention of the present invention.

An example of the device manufacturing process will now be described with reference to a flow chart of FIG. 11.

The manufacturing process includes the following main processes.

(1) A wafer manufacturing process for manufacturing a wafer (or wafer preparing process for preparing a wafer). (Step 600)

(2) A mask manufacturing process for fabricating a mask to be used in the exposure (or a mask preparing process). (Step 601)

(3) A wafer processing process for performing any processing treatments necessary for the wafer. (Step 602)

(4) A chip assembling process for cutting out those chips formed on the wafer one by one to make them operative. (Step 603)

(5) A chip inspection process for inspecting an assembled chip. (Step 604)

It is to be appreciated that each of those processes further comprises several sub-processes.

Among those main processes, the principal process that gives a critical affection to the performance of the semiconductor device is the wafer processing process. In this wafer processing process, the designed circuit patterns are stacked on the wafer one on another, thus to form many chips, which will function as memories and MPUs. This wafer processing process includes the following sub-processes.

(1) A thin film deposition process for forming a dielectric thin film to be used as an insulation layer and/or a metallic thin film to be formed into a wiring section or an electrode section, or the likes (by using the CVD process or the sputtering).

(2) An oxidizing process for oxidizing the formed thin film and/or the wafer substrate.

(3) A lithography process for forming a pattern of the resist by using a mask (reticle) in order to selectively process the thin film layer and/or the wafer substrate.

(4) An etching process for processing the thin film layer and/or the wafer substrate in accordance with the pattern of the resist (by using, for example, the dry etching technology).

(5) An ions/impurities implant and diffusion process.

(6) A resist stripping process.

(7) An inspection process for inspecting the processed wafer.

It should be noted that the wafer processing process must be performed repeatedly as desired depending on the number of layers contained in the wafer, thus to manufacture the device that will be able to operate as designed.

Figure 12:
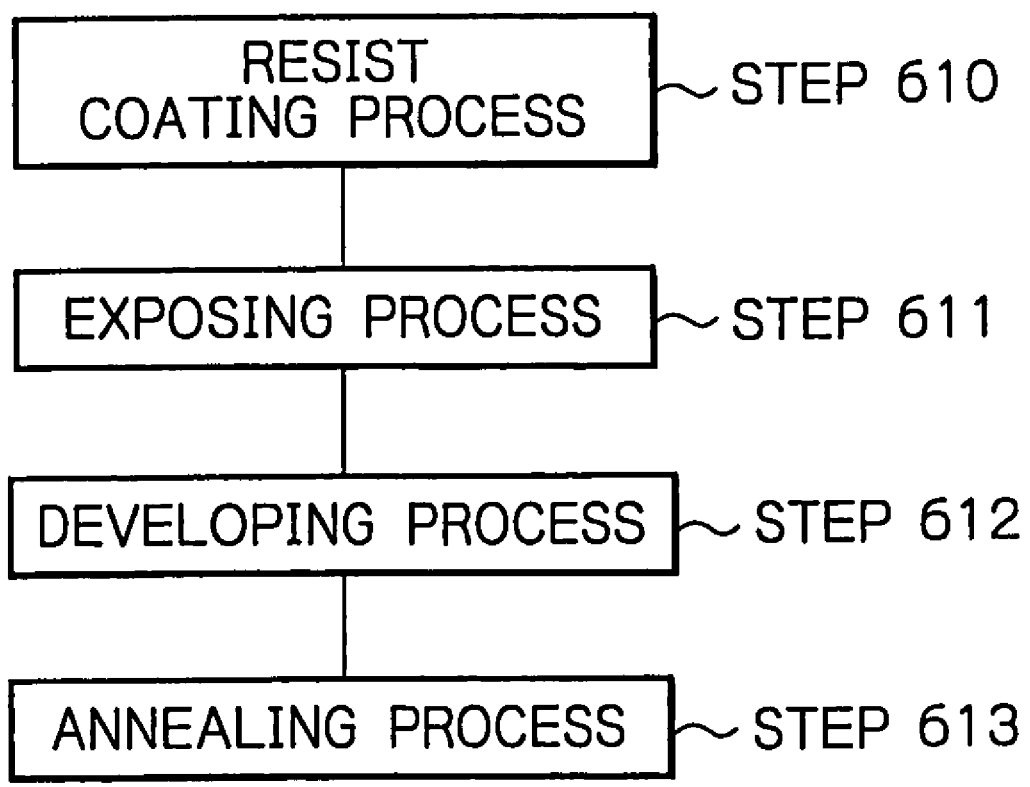
FIG. 12 is a flow chart showing a lithography process as a part of the semiconductor device manufacturing processes of FIG. 11.

FIG. 12 shows the lithography process included as a core process in said wafer processing process. The lithography process comprises the respective processes as described below.

(1) A resist coating process for coating the wafer having a circuit pattern formed thereon in the preceding stage with the resist. (Step 610)

(2) An exposing process for exposing the resist. (Step 611)

(3) A developing process for developing the exposed resist to obtain the pattern of the resist. (Step 612)

(4) An annealing process for stabilizing the developed pattern. (Step 613)

Known procedures may be applied to all of the semiconductor manufacturing process, the wafer processing process, and the lithography process described above.

When the electron beam apparatus according to the above-described respective embodiments is applied to the wafer inspection process (7) described above, such a semiconductor device having a minute pattern can be evaluated with high throughput and high precision, thus improving the yield of the products and prohibiting any defective products from being delivered.

According to the device manufacturing method of the sixth invention, since a wafer in the course of processing or after completion of the process can be evaluated reliably with a high throughput by using the electron beam apparatus described above, advantageously it becomes possible to improve a yield of products and to prevent defective products from being delivered.

The invention claimed is:

1. An electron beam apparatus for evaluating a sample surface comprising:
    an electron gun having a cathode and anode for emitting an electron beam and for focusing and irradiating the electron beam onto a sample surface;
    a detector for detecting secondary electron beams emanated from the sample surface;
    wherein the sample surface has a partial region which is providing a relatively weak region against dielectric breakdown being caused by irradiating the electron beam; and
    a controller for controlling the electron beam so as not to be irradiating the weak region, wherein the weak region has a gate oxide film of a transistor formed thereon and a electric connection with the region of the gate oxide film.

2. An electron beam apparatus according to claim 1, wherein said electron beam apparatus comprises an electron optical system which produces a decelerating electric field for a primary electron beam between an objective lens and said sample.

3. An electron beam apparatus according to claim 1, wherein scanning operation of the electron beam is adapted to be applied over an entire surface of the sample, while said electron beam may be blanked when said electron beam is to scan said region relatively weak against said dielectric breakdown.

4. An electron beam apparatus according to claim 1, wherein said secondary electrons emanated from an electron beam irradiated region on a surface of the sample are detected so as to evaluate the sample, wherein a surface of a sample is segmented into a region relatively weak against dielectric breakdown and the other regions, wherein small dose levels of the electron beam is applied to said respective weak regions so as to evaluate the surface of the sample.

5. A device manufacturing method, comprising:
preparing wafers;
processing the wafer;
evaluating said processed wafers using electron beam apparatus as claimed in claim 1;
repeating said last two steps; and
assembling devices using said processed wafers.

6. An electron beam apparatus for evaluating a sample surface comprising:
an electron gun having a cathode and anode for emitting an electron beam and for focusing and irradiating the electron beam onto a sample surface;
a detector for detecting secondary electron beam emanated from the sample surface; and
a controller for controlling the electron beam with a small dose level of the electron beam for a relatively weak region against dielectric breakdown being caused by irradiating the electron beam.

7. An electron beam apparatus according to claim 6, wherein said relatively weak region is a region having a gate oxide film of a transistor formed thereon and an electric connection of the gate oxide film.

8. A sample evaluation method comprising:
emitting an electron beam from an electron bun having a cathode and anode;
focusing and irradiating the electron beam onto a sample surface;
detecting secondary electron beam emanated from the sample surface;
specifying a partial region on said sample surface which is a relatively weak region against dielectric breakdown being caused by irradiating the electron beam, and
controlling the electron beam so as not to be irradiated onto said weak region.

9. A sample evaluation method comprising:
segmenting said sample into a region relatively weak against dielectric breakdown and the other region;
emitting an electron beam from an electron bun having a cathode and anode;
focusing and irradiating the electron beam onto a sample surface;
detecting secondary electron beam emanated from the sample surface and;
controlling said irradiation of the electron beam so that a small dose level of the electron beam is applied to said respective weak region so as to evaluate the surface of the sample.

* * * * *